US012029542B2

(12) United States Patent
Chun et al.

(10) Patent No.: US 12,029,542 B2
(45) Date of Patent: Jul. 9, 2024

(54) DISPLAY DEVICE

(71) Applicant: Samsung Display Co., Ltd., Yongin-si (KR)

(72) Inventors: Seungwook Chun, Daegu (KR); Yuna Kim, Seoul (KR); Yun-Ho Kim, Hwaseong-si (KR); Chul Kim, Hwaseong-si (KR); Soojung Lee, Suwon-si (KR); Boram Choi, Asan-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 0 days.

(21) Appl. No.: 17/357,949

(22) Filed: Jun. 24, 2021

(65) Prior Publication Data
US 2022/0087566 A1 Mar. 24, 2022

(30) Foreign Application Priority Data

Sep. 24, 2020 (KR) .................. 10-2020-0124274

(51) Int. Cl.
*G06F 3/041* (2006.01)
*A61B 5/0537* (2021.01)

(52) U.S. Cl.
CPC ........ *A61B 5/0537* (2013.01); *G06F 3/04164* (2019.05); *G06F 3/04166* (2019.05); *G06F 2203/04112* (2013.01)

(58) Field of Classification Search
None
See application file for complete search history.

(56) References Cited

U.S. PATENT DOCUMENTS 9,952,714 B2 4/2018 Yatsu et al.
10,209,842 B2 2/2019 Lee et al.
2006/0033626 A1* 2/2006 Collins .............. G08B 21/0211
340/573.1

(Continued)

FOREIGN PATENT DOCUMENTS

JP 2017-062744 3/2017
JP 6101123 3/2017
(Continued)

*Primary Examiner* — Krishna P Neupane
(74) *Attorney, Agent, or Firm* — Lewis Roca Rothgerber Christie LLP

(57) ABSTRACT

A display device includes a display panel, an input sensor, and a readout circuit. The display panel is configured to display an image. The input sensor is disposed on the display panel, and incudes transmission electrodes and reception electrodes electrically insulated from the transmission electrodes. The readout circuit is connected to the input sensor, and includes a first transmission/reception circuit, a second transmission/reception circuit, and a control circuit. The first transmission/reception circuit is electrically connected to the reception electrodes. The second transmission/reception circuit electrically is connected to the transmission electrodes. The control circuit configured to transmit a transmission signal to the input sensor through one of the first transmission/reception circuit and the second transmission/reception circuit, and to receive a reception signal from the input sensor through the other of the first transmission/reception circuit and the second transmission/reception circuit.

3 Claims, 24 Drawing Sheets

(56) References Cited

U.S. PATENT DOCUMENTS

| | | | |
|---|---|---|---|
| 2014/0104200 A1 | 4/2014 | Ahn et al. | |
| 2015/0185918 A1* | 7/2015 | Backman | G06F 3/04166 |
| | | | 345/174 |
| 2015/0234498 A1* | 8/2015 | Cho | G06F 3/0446 |
| | | | 345/174 |
| 2016/0147367 A1* | 5/2016 | Kim | G06F 3/011 |
| | | | 345/174 |
| 2016/0274726 A1* | 9/2016 | Chung | G06F 3/014 |
| 2017/0147103 A1* | 5/2017 | Han | G06F 1/1652 |
| 2017/0336909 A1* | 11/2017 | Song | G06F 3/04166 |
| 2020/0125231 A1* | 4/2020 | Sakoda | G06F 3/04166 |
| 2020/0326805 A1* | 10/2020 | Lee | G06F 3/0412 |

FOREIGN PATENT DOCUMENTS

| | | |
|---|---|---|
| JP | 2020-067733 | 4/2020 |
| KR | 10-1330320 | 11/2013 |
| KR | 10-2019776 | 9/2019 |

* cited by examiner

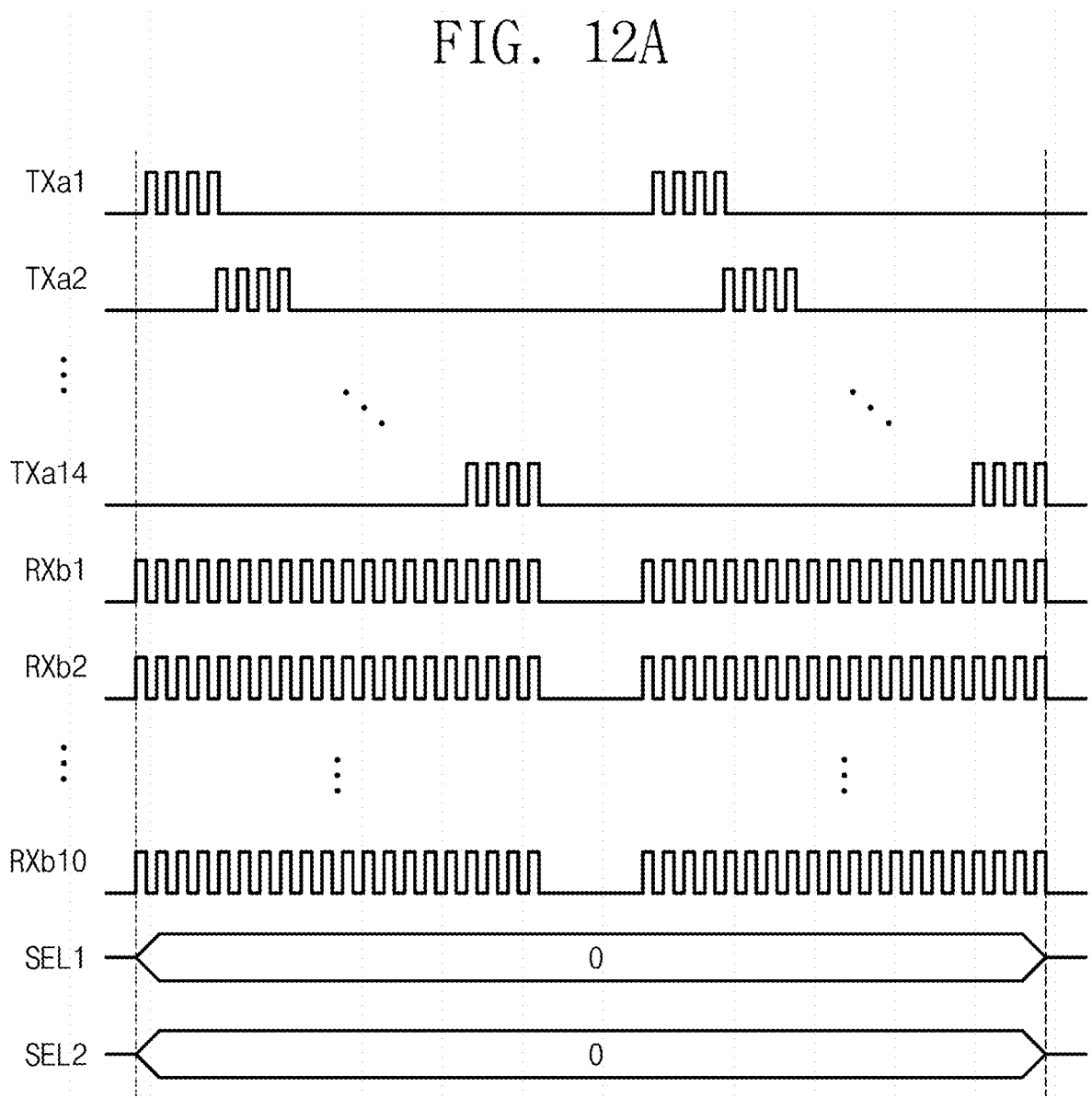

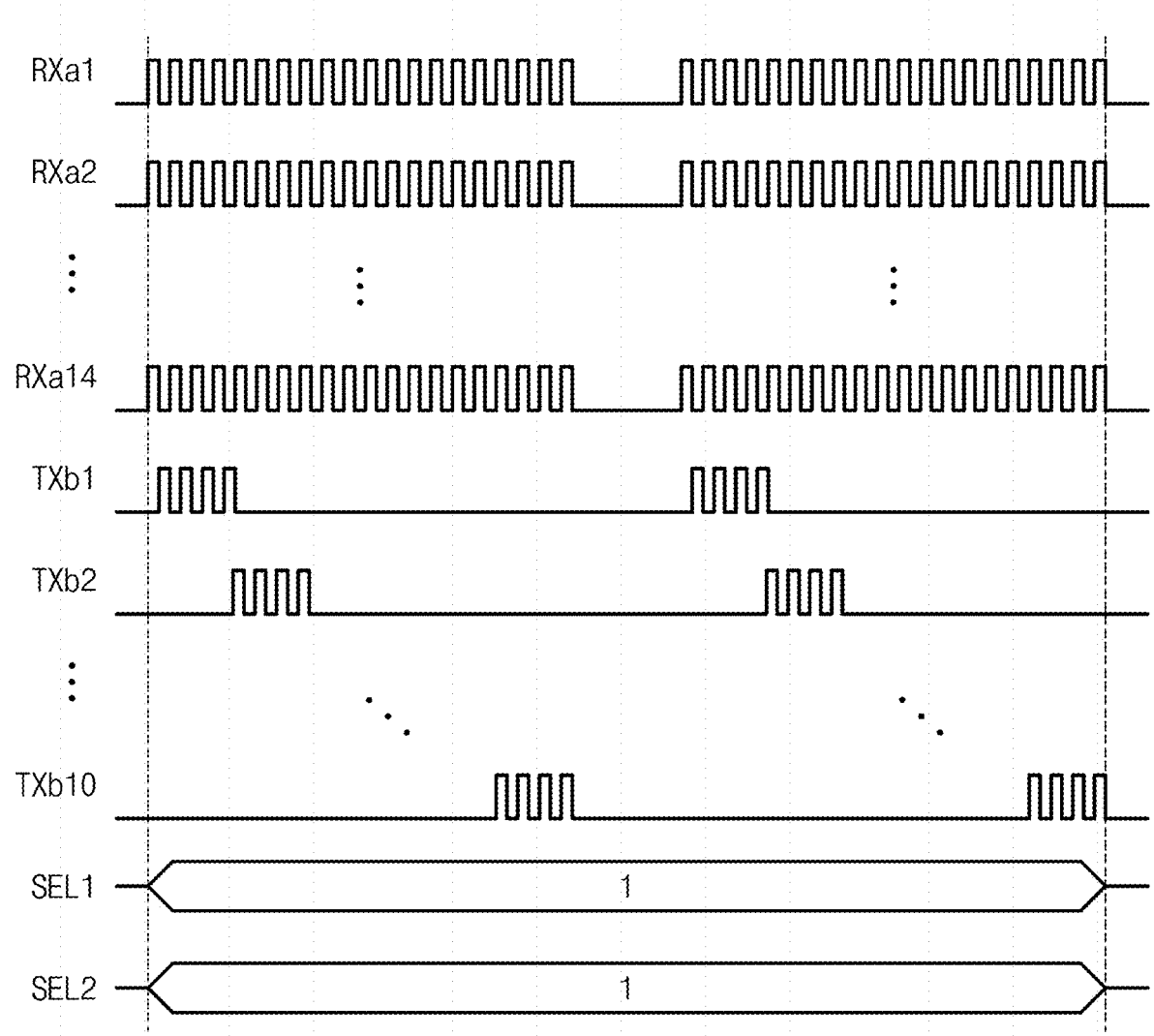

DISPLAY DEVICE

CROSS-REFERENCE TO RELATED APPLICATIONS

This application claims priority to and the benefit of Korean Patent Application No. 10-2020-0124274, filed Sep. 24, 2020, which is hereby incorporated by reference for all purposes as if fully set forth herein.

BACKGROUND

Field

Embodiments generally relate to a display device, and more particularly, to a display device including an input sensor capable of sensing a user input.

Discussion

Multimedia electronic devices, such as televisions, mobile phones, tablets, computers, navigation system units, game consoles, etc., may be equipped with a display device for displaying images. The electronic devices may include a display device that may provide a touch-based input method that allows a user to easily input information or commands intuitively and conveniently in addition to a typical input method, such as a button, a keyboard, a mouse, and/or the like. As a personal electronic device, such as a mobile phone, is widely used, a need for a display device having an input sensor capable of sensing various inputs, such as biometric information and pen input, as well as a user's touch has increased.

The above information disclosed in this section is only for understanding the backgrounds, and, therefore, may contain information that does not form prior art.

SUMMARY

Some aspects provide a display device capable of operating an input sensor in various modes.

Additional aspects will be set forth in the detailed description which follows, and, in part, will be apparent from the disclosure, or may be learned by practices.

According to an embodiment, a display device includes a display panel, an input sensor, and a readout circuit. The display panel is configured to display an image. The input sensor is disposed on the display panel, and incudes transmission electrodes and reception electrodes electrically insulated from the transmission electrodes. The readout circuit is connected to the input sensor, and includes a first transmission/reception circuit, a second transmission/reception circuit, and a control circuit. The first transmission/reception circuit is electrically connected to the reception electrodes. The second transmission/reception circuit electrically is connected to the transmission electrodes. The control circuit configured to transmit a transmission signal to the input sensor through one of the first transmission/reception circuit and the second transmission/reception circuit, and to receive a reception signal from the input sensor through the other of the first transmission/reception circuit and the second transmission/reception circuit.

According to an embodiment, a display device includes a display panel, an input sensor, and a readout circuit. The display panel is configured to display an image. The input sensor is disposed on the display panel, and incudes transmission electrodes and reception electrodes electrically insulated from the transmission electrodes. The readout circuit is connected to the input sensor, and includes a first transmission/reception circuit, a second transmission/reception circuit, and a control circuit. The first transmission/reception circuit is electrically connected to the reception electrodes. The second transmission/reception circuit electrically is connected to the transmission electrodes. The control circuit is, in a body composition measurement mode, configured to transmit a transmission signal to some of the transmission electrodes through the second transmission/reception circuit, and to receive a reception signal from some of the reception electrodes through the first transmission/reception circuit.

According to an embodiment, a display device includes a display panel, an input sensor, and a readout circuit. The display panel is configured to display an image. The input sensor is disposed on the display panel, and incudes transmission electrodes and reception electrodes electrically insulated from the transmission electrodes. The readout circuit is connected to the input sensor, and includes a first transmission/reception circuit, a second transmission/reception circuit, and a control circuit. The first transmission/reception circuit is electrically connected to the reception electrodes. The second transmission/reception circuit electrically is connected to the transmission electrodes. The control circuit is, in a body composition measurement mode, configured to transmit a transmission signal to a first some of the reception electrodes through the first transmission/reception circuit, and to receive a reception signal from a second some of the reception electrodes through the first transmission/reception circuit, the second some of the reception electrodes being different from the first some of the reception electrodes.

It is to be understood that both the foregoing general description and the following detailed description are illustrative and explanatory and are intended to provide further explanation of the invention as claimed.

BRIEF DESCRIPTION OF THE DRAWINGS

The accompanying drawings, which are included to provide a further understanding of the inventive concepts, and are incorporated in and constitute a part of this specification, illustrate exemplary embodiments of the inventive concepts, and, together with the description, serve to explain principles of the inventive concepts. In the drawings:

FIGS. 12A, 12B, 12C, and 12D are timing diagrams showing first transmission signals, second transmission signals, first reception signals, and second reception signals in first to fourth operation modes according to various embodiments;

DETAILED DESCRIPTION OF SOME EMBODIMENTS

Figure 1:
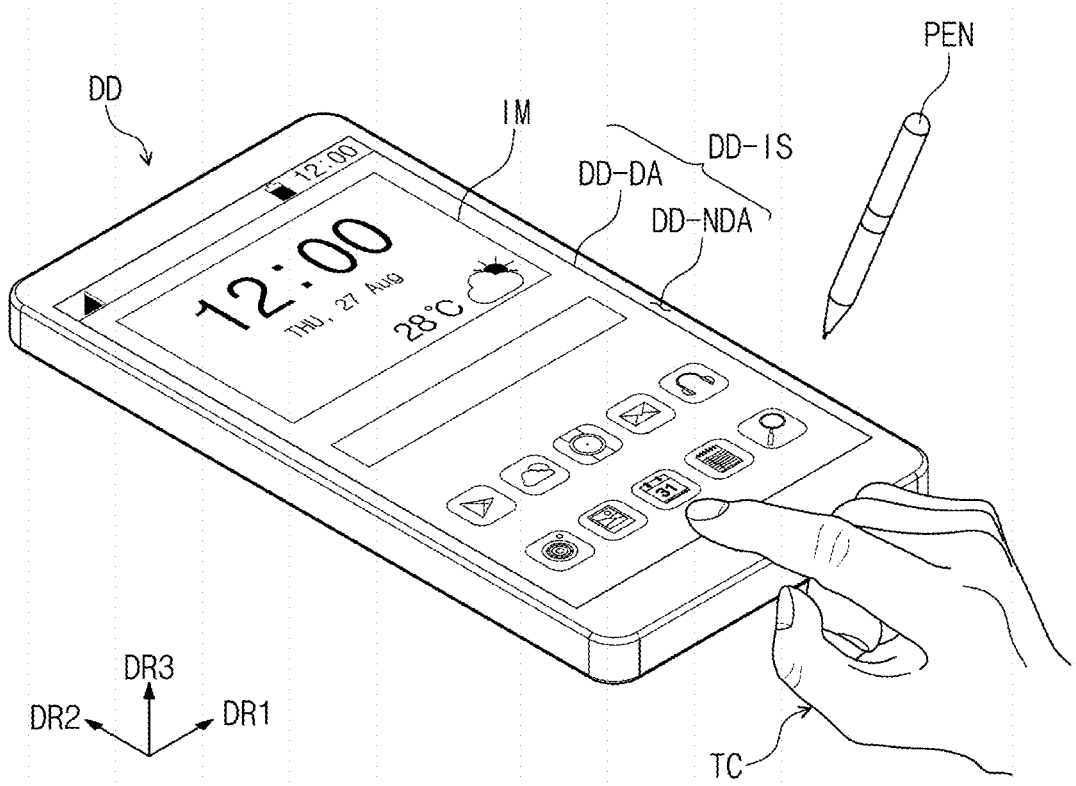
FIG. 1 is a perspective view of a display device according to an embodiment.

In the following description, for the purposes of explanation, numerous specific details are set forth in order to provide a thorough understanding of various embodiments or implementations. As used herein, the terms "embodiments" and "implementations" may be used interchangeably and are non-limiting examples employing one or mores disclosed herein. It is apparent, however, that various embodiments may be practiced without these specific details or with one or more equivalent arrangements. In other instances, well-known structures and devices are shown in block diagram form to avoid unnecessarily obscuring various embodiments. Further, various embodiments may be different, but do not have to be exclusive. For example, specific shapes, configurations, and characteristics of an embodiment may be used or implemented in another embodiment without departing from the inventive concepts.

Unless otherwise specified, the illustrated embodiments are to be understood as providing example features of varying detail of some embodiments. Therefore, unless otherwise specified, the features, components, modules, layers, films, panels, regions, aspects, etc. (hereinafter individually or collectively referred to as an "element" or "elements"), of the various illustrations may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. As such, the sizes and relative sizes of the respective elements are not necessarily limited to the sizes and relative sizes shown in the drawings. When an embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element, it may be directly on, connected to, or coupled to the other element or intervening elements may be present. When, however, an element is referred to as being "directly on," "directly connected to," or "directly coupled to" another element, there are no intervening elements present. Other terms and/or phrases used to describe a relationship between elements should be interpreted in a like fashion, e.g., "between" versus "directly between," "adjacent" versus "directly adjacent," "on" versus "directly on," etc. Further, the term "connected" may refer to physical, electrical, and/or fluid connection. In addition, the X-axis, the Y-axis, and the Z-axis are not limited to three axes of a rectangular coordinate system, and may be interpreted in a broader sense. For example, the X-axis, the Y-axis, and the Z-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and/or the like, may be used herein for descriptive purposes, and, thereby, to describe one element's relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing some embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various embodiments are described herein with reference to sectional views, isometric views, perspective views, plan views, and/or exploded illustrations that are schematic illustrations of idealized embodiments and/or intermediate structures. As such, variations from the shapes of the illustrations as a result of, for example, manufacturing techniques and/or tolerances, are to be expected. Thus, embodiments disclosed herein should not be construed as limited to the particular illustrated shapes of regions, but are to include deviations in shapes that result from, for instance, manufacturing. To this end, regions illustrated in the drawings may be schematic in nature and shapes of these regions may not reflect the actual shapes of regions of a device, and, as such, are not intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and will not be interpreted in an idealized or overly formal sense, unless expressly so defined herein.

Hereinafter, various embodiments will be explained in detail with reference to the accompanying drawings.

FIG. 1 is a perspective view of a display device DD according to an embodiment.

As shown in FIG. 1, the display device DD may display an image IM through a display surface DD-IS. The display surface DD-IS is parallel to a plane defined by a first direction axis DR1 and a second direction axis DR2. A normal direction of the display surface DD-IS, e.g., a thickness direction of the display device DD, is indicated by a third direction axis DR3.

A front surface (or an upper surface) and a back surface (or a lower surface) of each component or member described hereinafter are distinguished by the third direction axis DR3. However, the first to third direction axes DR1, DR2, and DR3 are merely illustrative. In addition, first to third directions are defined as directions indicated by the first to third direction axes DR1, DR2, DR3, respectively, and are given the same reference numerals.

In an embodiment, the display device DD is provided with a planar display surface; however, embodiments are not limited thereto. The display device DD may further include a curved display surface. The display device DD may include a three-dimensional display surface. The three-dimensional display surface may include a plurality of display regions indicating different directions, and may include, for example, a polygonal column type display surface.

The display device DD according to an embodiment may be a rigid display device; however, embodiments are not limited thereto. The display device DD according to an embodiment may be a flexible display device. The flexible display device may include a foldable display device capable of being folded or a bending-type display device in which some regions thereof are bent, and a slidable display device.

In an embodiment, the display device DD may be applicable to a cellphone terminal and is illustrated as an example in FIG. 1. Electronic modules, a camera module, a power module, and/or the like may be mounted on a main board and may be disposed in a bracket/case and/or the like together with the display device DD to configure the cellphone terminal. The display device DD; however, may be applicable to large-sized electronic devices, such as televisions, monitors, etc., and also to small-and-medium-sized electronic devices, such as tablets, car navigation systems, game consoles, smart watches, and/or the like.

As shown in FIG. 1, the display surface DD-IS includes an image region DD-DA on (or in) which the image IM is displayed, and a bezel (or peripheral) region DD-NDA adjacent to (or outside) the image region DD-DA. The bezel region DD-NDA is a region on which an image is not displayed. In FIG. 1, as an example of the image IM, a clock, weather information, and application icons are illustrated.

As shown in FIG. 1, the image region DD-DA may have substantially a quadrangular shape. The term "substantially a quadrangular shape" includes not only a quadrangular shape in a mathematical sense, but also includes a quadrangular shape in which no vertex is defined in a vertex region (or corner region), but a curved boundary is defined.

The bezel region DD-NDA may surround the image region DD-DA; however, embodiments are not limited thereto. The shape of the image region DD-DA and the shape of the bezel region DD-NDA may be designed to have different shapes. The bezel region DD-NDA may be disposed on only one side of the image region DD-DA. Depending on the coupling form of the display device DD and other components of an electronic device, the bezel region DD-NDA may not be exposed to the outside.

The display device DD according to an embodiment may sense a user input TC applied from the outside. The display device DD may sense the user input TC by sensing a change in at least one of reflected light, temperature, pressure, ultrasonic waves, and electromagnetic waves by the user input TC, or any combination thereof. In an embodiment, the user input TC is assumed and described to be a touch input by a user's hand applied to a front surface FS of the display device DD; however, this is merely illustrative and other forms of inputs (e.g., hovering inputs, approaching inputs, etc.) and other portions of a user's person (e.g., arm, eyes, face, foot, etc.) are contemplated. As described above, the user input TC may be provided in various forms. In addition, depending on the structure of the display device DD, the display device DD may sense the user input TC applied to a side surface or a back surface of the display device DD, and is not limited to any one embodiment.

In addition, the display device DD according to an embodiment may sense an input by an electronic pen PEN or other suitable object. The electronic pen PEN may be an input device using a mechanism, such as a stylus pen, an electronic pen, an active pen, etc.

Figure 2:
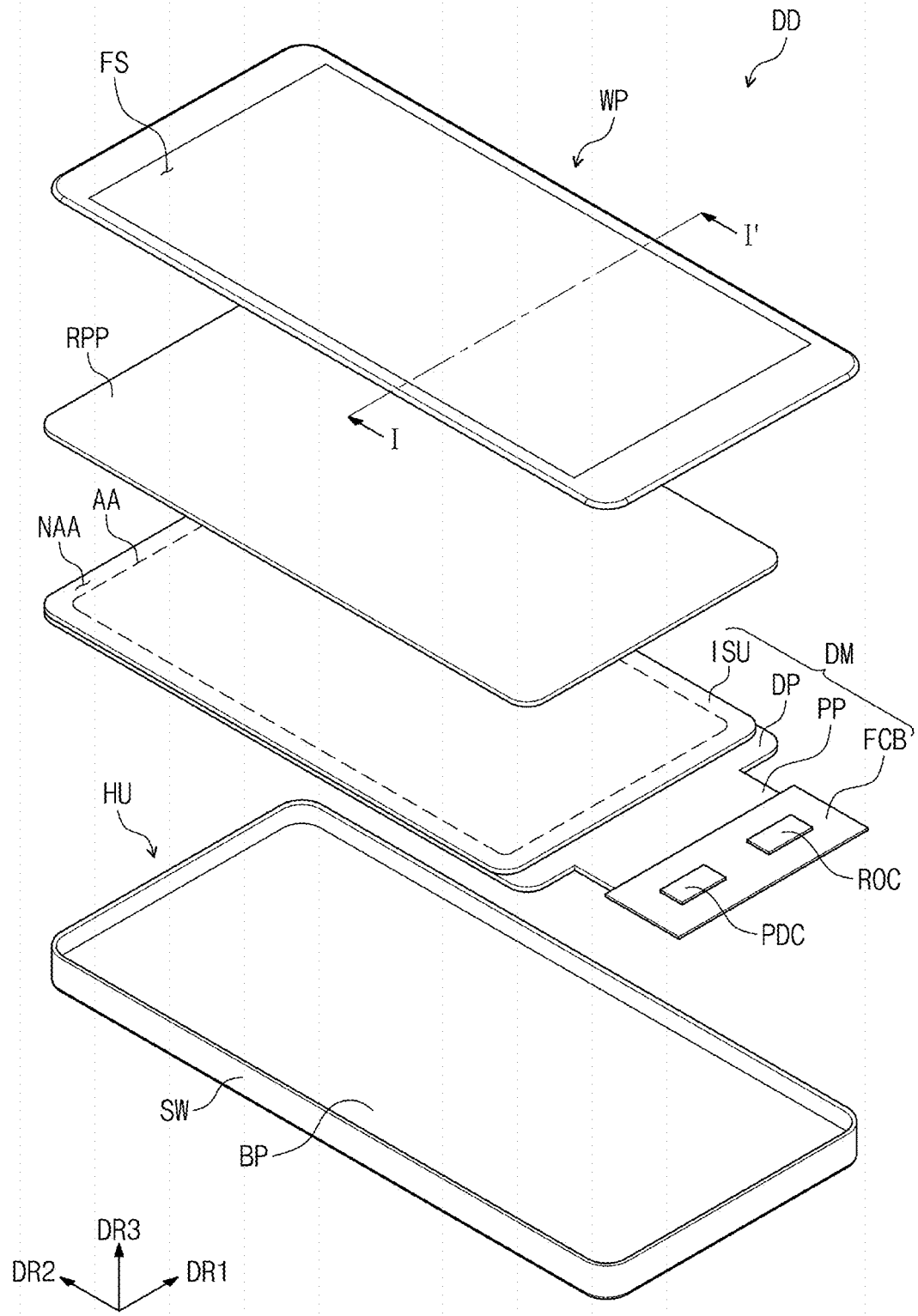
FIG. 2 is an exploded perspective view of a display device according to an embodiment.

FIG. 2 is an exploded perspective view of a display device according to an embodiment.

Referring to FIG. 2, the display device DD may include a window WP, an anti-reflector RPP, a display module DM, and a housing HU. As illustrated in FIGS. 1 and 2, in an embodiment, the window WP and the housing HU are coupled to configure the appearance of the display device DD.

The window WP protects an upper surface of a display module DM. The window WP may include an optically transparent insulation material. In an embodiment, the window WP may include a front surface FS including at least one of glass and plastic. The window WP may have a multi-layered structure or a single-layered structure. For example, the window WP may include a plurality of plastic films coupled with an adhesive, or a glass substrate and a plastic film coupled with an adhesive.

The anti-reflector RPP may be disposed below the window WP. The anti-reflector RPP reduces the reflectance of external light incident from an upper side of the window WP. In an embodiment, the anti-reflector RPP may be omitted, or may be embedded inside (or as part of) the display module DM.

The display module DM may display the image IM and sense an external input. The display module DM may include a display panel DP, an input sensor ISU, and a printed circuit board FCB.

An active region AA and a peripheral region NAA corresponding to the image region DD-DA and the bezel region DD-NDA illustrated in FIG. 1 may be defined in the display panel DP. The display panel DP may be a component that substantially generates the image IM. The image IM generated by the active region AA of the display panel DP is visible to a user from the outside through the window WP. It is also contemplated that at least one of the active region AA and the peripheral region NAA may not correspond (e.g., made be shaped, sized, etc.) differently than at lasts one of the image region DD-DA and the bezel region DD-NDA.

The input sensor ISU senses an external input applied from the outside. As described above, the input sensor ISU may sense an external input provided to the window WP.

The display panel DP may be electrically connected to the printed circuit board FCB. In an embodiment, a driving chip that generates signals for operation of the display panel DP may be mounted on the display panel DP, but embodiments are not limited thereto. The printed circuit board FCB may include various driving circuits for driving the display panel DP and the input sensor ISU, a connector for supplying power, and/or the like. In an embodiment, the printed circuit board FCB may include a panel driving circuit PDC for driving the display panel DP and a readout circuit ROC for driving the input sensor ISU. Each of the panel driving circuit PDC and the readout circuit ROC may be formed as an integrated circuit and mounted on the printed circuit board FCB. In another embodiment, the panel driving circuit PDC and the readout circuit ROC may be formed as one integrated circuit.

The housing HU includes a bottom portion BP and a sidewall SW. The sidewall SW may be extended from the bottom portion BP. The housing HU may accommodate the display panel DP in an accommodation space defined by the bottom portion BP and the sidewall SW. The window WP may be coupled to the sidewall SW of the housing HU. The sidewall SW of the housing HU may support an edge of the window WP.

The housing HU may include a material having relatively high rigidity. For example, the housing HU may include at least one of glass, plastic, and a metal, or may include a plurality of frames and/or plates composed of a combination thereof. The housing HU may stably protect components of the display device DD accommodated in the internal space from an external impact.

Figure 3:
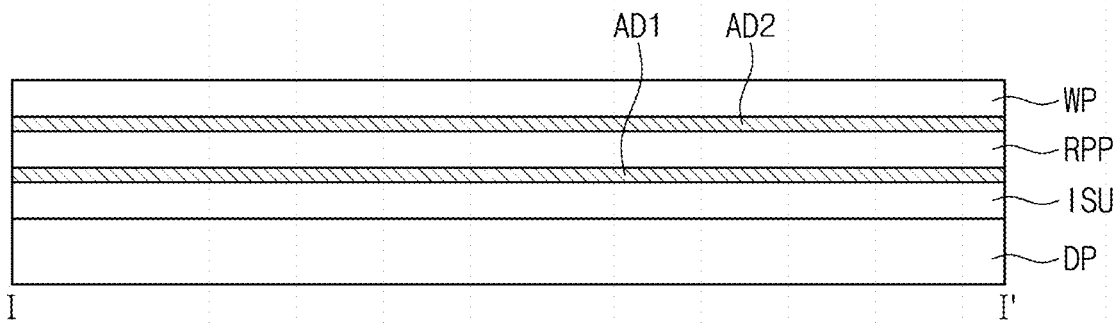
FIG. 3 is a cross-sectional view taken along sectional line I-I' illustrated in FIG. 2 according to an embodiment.

FIG. 3 is a cross-sectional view taken along sectional line I-I' illustrated in FIG. 2 according to an embodiment.

FIG. 3 illustrates a cross-section of the display device DD defined by the first direction axis DR1 and the third direction axis DR3. In FIG. 3, components of the display device DD are simply illustrated to describe the lamination relationship thereof.

The display device DD according to an embodiment may include the display panel DP, the input sensor ISU, the anti-reflector RPP, and the window WP. At least some of the display panel DP, the input sensor ISU, the anti-reflector RPP, and the window WP may be formed in a series of processes, or at least some thereof may be coupled to each other through an adhesive member. For example, the input sensor ISU and the anti-reflector RPP may be coupled by an adhesive member AD1. The anti-reflector RPP and the window WP may be coupled by an adhesive member AD2.

The adhesive members AD1 and AD2 may be transparent adhesive members, such as a pressure sensitive adhesive film (PSA), an optically clear adhesive film (OCA), or an optically clear resin (OCR). The adhesive member described hereinafter may include a typical adhesive or a pressure-sensitive adhesive. In an embodiment, the anti-reflector RPP and the window WP may be replaced by other components or may be omitted.

In FIG. 3, among the input sensor ISU, the anti-reflector RPP, and the window WP, the input sensor ISU (formed through a series of processes with the display panel DP) is directly disposed on the display panel DP. In this disclosure, "a component B is directly disposed on a component A" means that no separate adhesive layer/adhesive member is disposed between the component A and the component B. After the component A is formed, the component B is formed through a series of processes on a base surface provided by the component A.

In an embodiment, the anti-reflector RPP and the window WP are a "panel" type, and the input sensor ISU is a "layer" type. The "panel" type includes a base layer that provides a base surface, for example, a synthetic resin film, a composite film, a glass substrate, and/or the like, but the "layer" type may not include the base layer. In other words, components of the "layer" type are directly disposed on a base surface provided by another component. In an embodiment, the anti-reflector RPP and the window WP may be the "layer" type. In an embodiment, the input sensor ISU may be a "panel" type.

The display panel DP generates an image, and the input sensor ISU obtains the coordinate information of an external input (for example, a touch event). The display device DD according to an embodiment may further include a protective member disposed on a lower surface (or a rear surface) of the display panel DP. The protective member and the display panel DP may be coupled through an adhesive member.

The display panel DP according to an embodiment may be a light-emitting type display panel, but is not limited thereto. For example, the display panel DP may be an organic light-emitting display panel, a quantum dot light-emitting display panel, etc. The panels are distinguished according to the constituent materials of light-emitting elements. A light-emitting layer of an organic light-emitting display panel may include an organic light-emitting material. A light-emitting layer of a quantum dot light-emitting display panel may include quantum dots and/or quantum rods, and/or the like.

Hereinafter, the display panel DP will be described as an organic light-emitting display panel.

The anti-reflector RPP reduces the reflectance of external light incident from an upper side of the window WP. The anti-reflector RPP according to an embodiment may include at least one of a phase retarder and a polarizer. The phase retarder may be of a film type or a liquid crystal coating type. The polarizer may also be of a film type or a liquid crystal coating type. A film type polarizer may include an extensible synthetic resin film, and a liquid crystal coating type polarizer may include liquid crystals arranged in a predetermined arrangement. The phase retarder and the polarizer may further include a protective film. The phase retarder and the polarizer themselves, or the protective film may be defined as a base layer of the anti-reflector RPP.

The anti-reflector RPP according to an embodiment may include color filters. The color filters have a predetermined arrangement. The arrangement of the color filters may be determined in consideration of the light emitting colors of pixels included in the display panel DP. The anti-reflector RPP may further include a black matrix adjacent to the color filters.

The anti-reflector RPP according to an embodiment may include a destructive interference structure. In an embodiment, the destructive interference structure may include a first reflective layer and a second reflective layer disposed on different layers. First reflective light and second reflective light respectively reflected from the first reflective layer and the second reflective layer may be destructively interfered, and accordingly, the reflectance of external light is reduced.

The window WP according to an embodiment may include a glass substrate and/or a synthetic resin film, and/or the like. The window WP is not limited to a single layer. The window WP may include two or more films coupled with an adhesive member. Although not separately illustrated, the window WP may further include a functional coating layer. The functional coating layer may include at least one of an anti-fingerprint layer, an anti-reflection layer, a hard coating layer, and/or the like.

The input sensor ISU and the display panel DP will be described in more detail hereinafter.

Figure 4:
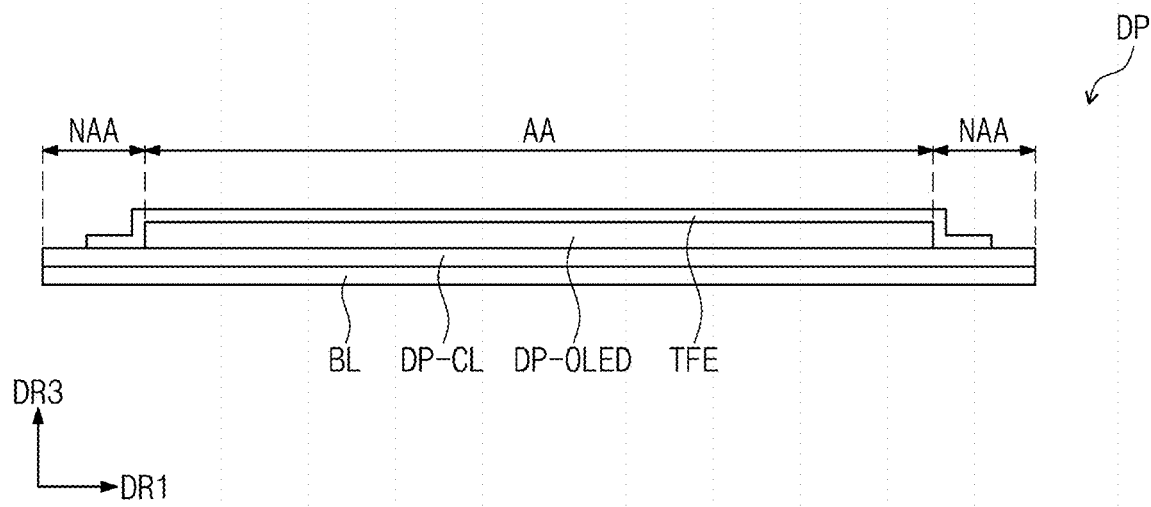
FIG. 4 is a cross-sectional view of a display panel illustrated in FIG. 3 according to an embodiment.

FIG. 4 is a cross-sectional view of the display panel DP shown in FIG. 3 according to an embodiment.

As illustrated in FIG. 4, the display panel DP includes a base layer BL, a circuit element layer DP-CL disposed on the base layer BL, a light emitting element layer DP-OLED, and a thin film encapsulation layer TFE. The active region AA and the peripheral region NAA corresponding to the image region DD-DA and the bezel region DD-NDA illustrated in FIG. 1 may be defined in the display panel DP. As used herein, the sentence "a region/portion corresponds to a region/portion" means "they overlap each other," but is not limited to having the same area and/or the same shape.

The base layer BL may include at least one synthetic resin film. The base layer BL may include at least one of a glass substrate, a metal substrate, an organic/inorganic composite material substrate, or the like.

On the base layer BL, the circuit element layer DP-CL is disposed. The circuit element layer DP-CL includes at least one insulation layer and circuit elements. The insulation layer includes at least one inorganic layer and at least one organic layer. The circuit elements may include signal lines, a pixel driving circuit, and/or the like.

On the circuit element layer DP-CL, the light emitting element layer DP-OLED is disposed. The light emitting element layer DP-OLED may include organic light emitting diodes. The light emitting element layer DP-OLED may further include an organic layer, such as a pixel definition film or layer.

The thin film encapsulation layer TFE may be disposed on the light emitting element layer DP-OLED and encapsulate the light emitting element layer DP-OLED. The thin film encapsulation layer TFE may cover the entire active region AA. The thin film encapsulation layer TFE may cover a portion of the peripheral region NAA.

The thin film encapsulation layer TFE includes a plurality of thin films. Some of the thin films are disposed to improve optical efficiency, and some of the thin films are disposed to protect the organic light emitting diodes.

Figure 5:
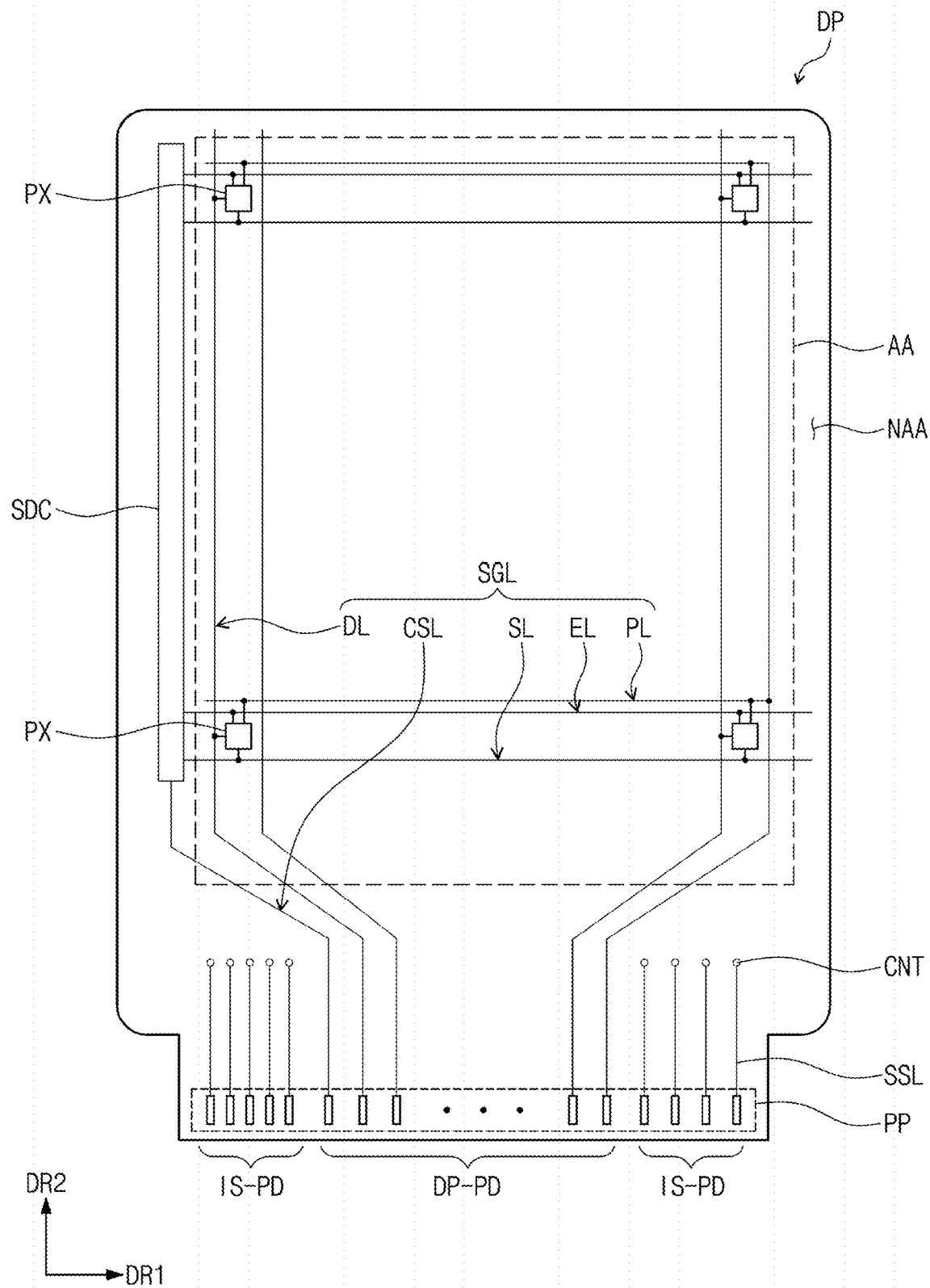
FIG. 5 is a plan view of a display panel according to an embodiment.

FIG. 5 is a plan view of the display panel DP according to an embodiment.

As illustrated in FIG. 5, the display panel DP may include a scan driving circuit SDC, a plurality of signal lines SGL (hereinafter, signal lines), a plurality of signal pads DP-PD and IS-PD (hereinafter, signal pads), and a plurality of pixels PX (hereinafter, pixels).

The scan driving circuit SDC generates a plurality of scan signals (hereinafter, scan signals), and sequentially outputs the scan signals to a plurality of scan lines SL (hereinafter, scan lines) to be described later. The scan driving circuit SDC may output other control signals, as well as scan signals to the pixels PX.

The scan driving circuit SDC may include a plurality of transistors (hereinafter, transistors) formed through a same process(es) as transistors in the pixels PX.

The signal lines SGL include scan lines SL, data lines DL, a power line PL, a light emission control line EL, and a control signal line CSL. Each of the scan lines SL, the data lines DL, and the light emission control lines EL are connected to a corresponding pixel PX among the pixels PX. The power line PL is commonly connected to the pixels PX. The control signal line CSL may provide control signals to the scan driving circuit SDC. The power line PL may provide a voltage for operation of the pixels PX. The power line PL may include a plurality of lines that provide different voltages.

In an embodiment, the signal lines SGL may further include auxiliary lines SSL. In an embodiment, the auxiliary lines SSL may be omitted. The auxiliary lines SSL are respectively connected to contact holes CNT. The auxiliary lines SSL may be electrically connected to signal lines of the input sensor ISU (refer to FIG. 6) to be described later through the contact holes CNT.

The display panel DP may include a pad region PP. In the pad region PP of the display panel DP, the plurality of signal pads DP-PD and IS-PD (refer to FIG. 5) may be disposed. The signal pads DP-PD and IS-PD may include first-type signal pads DP-PD connected to the data lines DL, the power line PL, and the control signal line CSL and second-type signal pads IS-PD connected to the auxiliary lines SSL. The first-type signal pads DP-PD and the second-type signal pads IS-PD are disposed adjacent to each other in the pad region PP defined in a portion of the peripheral region NAA. The laminate structure or constituent materials of the signal pads DP-PD and IS-PD may not be distinguished from each other, and may be formed through the same process.

The active region AA may be defined as a region in which the pixels PX are disposed. In the active region AA, a plurality of electronic elements is disposed. The electronic elements include, for instance, an organic light emitting diode provided in each of the pixels PX and a pixel driving circuit connected to the organic light emitting diode. The scan driving circuit SDC, the signal lines SGL, the signal pads DP-PD and IS-PD, and the pixel driving circuit may be included in the circuit element layer DP-CL illustrated in FIG. 4.

Each of the pixels PX may include a plurality of transistors, a capacitor, and an organic light emitting diode. The pixels PX emit light in response to signals received through the scan lines SL, the data lines DL, the light emission control lines EL, and the power line PL.

The signal pads DP-PD and IS-PD of the display panel DP may be electrically connected to the printed circuit board FCB illustrated in FIG. 2.

The display panel DP illustrated in FIG. 4 may be partially bent. A portion of the peripheral region NAA of the display panel DP may be bent, and may be bent based on a bending axis parallel to, for instance, the first direction DR1. The bending axis may be defined to overlap some of the data lines DL and some of the auxiliary lines SSL.

Figure 6:
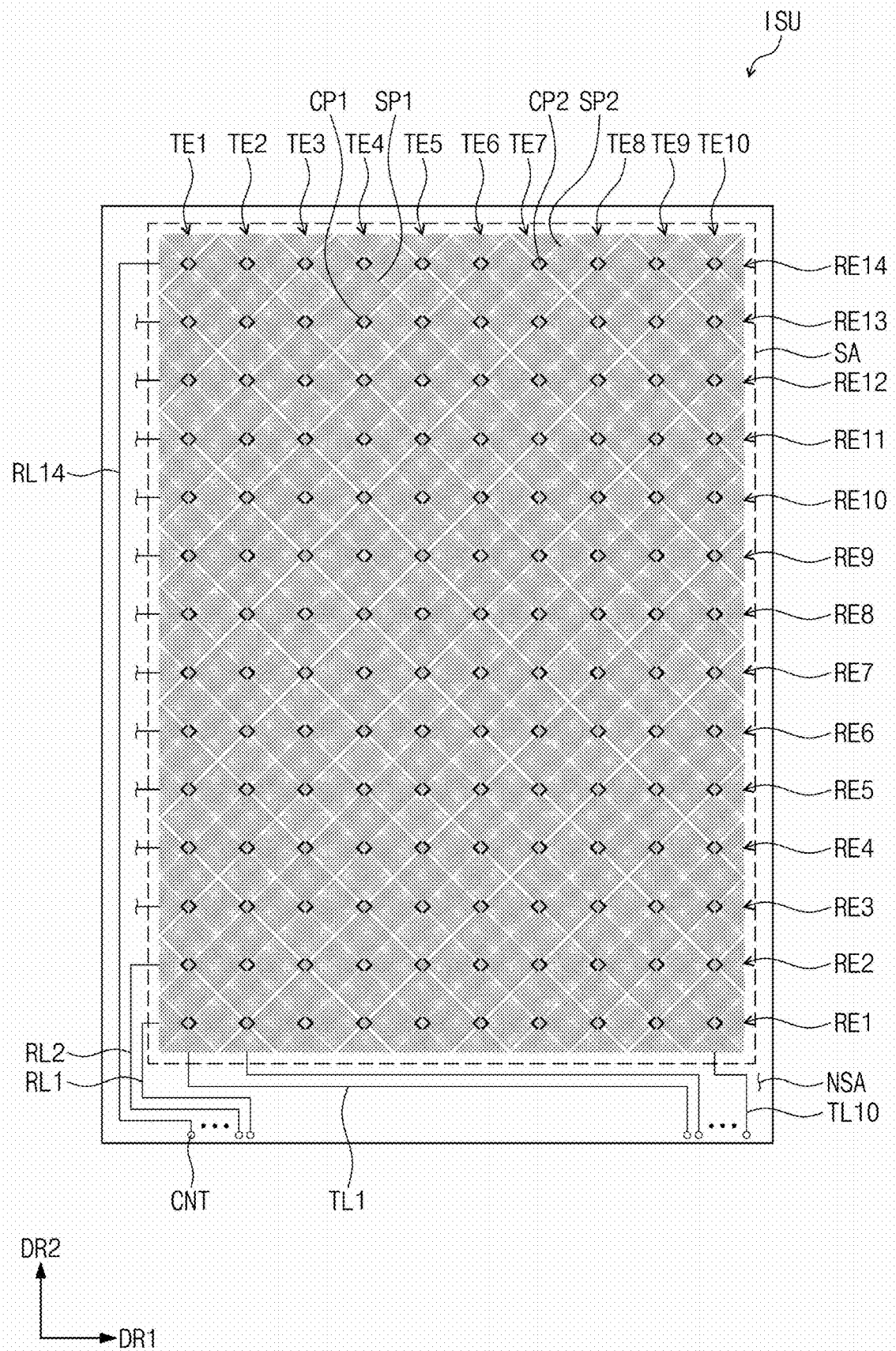
FIG. 6 is a plan view showing a configuration of an input sensor according to an embodiment.

FIG. 6 is a plan view showing a configuration of the input sensor ISU according to an embodiment.

Referring to FIG. 6, the input sensor ISU may include a sensing region SA and a non-sensing region NSA. The sensing region SA may be a region activated according to an electrical signal. In an embodiment, the sensing region SA may be a region that senses an input. The non-sensing region NSA may surround the sensing region SA. The sensing region SA may correspond to the active region AA of FIG. 5, and the non-sensing region NSA may correspond to the peripheral region NAA of FIG. 5.

The input sensor ISU includes transmission electrodes TE1 to TE10 and reception electrodes RE1 to RE14. The transmission electrodes TE1 to TE10 and the reception electrodes RE1 to RE14 are disposed in the sensing region SA. The transmission electrodes TE1 to TE10 and the reception electrodes RE1 to RE14 are electrically insulated from each other in the sensing region SA and intersect. As an example, the input sensor ISU includes first to tenth transmission electrodes TE1 to TE10 and first to fourteenth reception electrodes RE1 to RE14, but embodiments are not limited thereto. The number of the transmission electrodes and the number of the reception electrodes may vary. FIG. 6 illustrates that the number of reception electrodes is larger than the number of transmission electrodes; however, in another embodiment, the number of transmission electrodes may be larger than or the same as the number of reception electrodes.

In this disclosure, to clearly distinguish electrodes TE1 to TE10 from electrodes RE1 to RE14, the electrodes TE1 to TE10 are named as transmission electrodes and the electrodes RE1 to RE14 are named as reception electrodes. The functions of the electrodes, however, are not limited to the names of the electrodes. According to an operation mode, the transmission electrodes TE1 to TE10 may operate not only as transmission electrodes, but also as reception electrodes, and the reception electrodes RE1 to RE14 may operate not only as reception electrodes, but also as transmission electrodes.

Each of the first to tenth transmission electrodes TE1 to TE10 is extended in the second direction DR2. The first to tenth transmission electrodes TE1 to TE10 may be spaced apart from each other in the first direction DR1. The transmission electrodes TE1 to TE10 may be electrically separated from each other. Each of the first to tenth transmission electrodes TE1 to TE10 includes first sensing patterns SP1 spaced apart from one another in the first direction DR1 and first connecting patterns CP1 that electrically connect the first sensing patterns SP1. The first sensing patterns SP1 and the first connecting patterns CP1 are disposed on different layers, and do not have an integral shape.

Each of the first to fourteenth reception electrodes RE1 to RE14 extends in the first direction DR1. The first to fourteenth reception electrodes RE1 to RE14 may be spaced apart from each other in the second direction DR2. The first to fourteenth reception electrodes RE1 to RE14 may be electrically separated from each other. The first to fourteenth reception electrodes RE1 to RE14 are disposed intersecting the transmission electrodes TE1 to TE10, and may be electrically insulated from the transmission electrodes TE1 to TE10. Each of the first to fourteenth reception electrodes RE1 to RE14 includes second sensing patterns SP2 spaced apart from one another in the first direction DR1 and second connecting patterns CP2 that electrically connect the second sensing patterns SP2. The second sensing patterns SP2 and the second connecting patterns CP2 may have an integral shape.

FIG. 6 illustrates the first sensing patterns SP1 and the second sensing patterns SP2 each in a rhombic shape, but embodiments are not limited thereto. The first sensing patterns SP1 and the second sensing patterns SP2 may have shapes (e.g., polygonal shapes) different from each other.

Each of the first to tenth transmission electrodes TE1 to TE10 and each of the first to fourteenth reception electrodes RE1 to RE14 may have a mesh shape. Since each of the first to tenth transmission electrodes TE1 to TE10 and each of the first to fourteenth reception electrodes RE1 to RE14 have a mesh shape, parasitic capacitance with signal lines of the display panel DP (refer to FIG. 5) may be reduced.

The input sensor ISU may obtain position information on an external input through the change in mutual capacitance between the first to tenth transmission electrodes TE1 to TE10 and the first to fourteenth reception electrodes RE1 to RE14.

The input sensor ISU may further include first to tenth transmission lines TL1 to TL10 and first to fourteenth reception lines RL1 to RL14. The first to tenth transmission lines TL1 to TL10 and the first to fourteenth reception lines RL1 to RL14 may be disposed in the non-sensing region NSA. The first to tenth transmission lines TL1 to TL10 are electrically connected to one side of the first to tenth transmission electrodes TE1 to TE10, and the first to fourteenth reception lines RL1 to RL14 are electrically connected to one side of the first to fourteenth reception electrodes RE1 to RE14. However, embodiments are not limited thereto. As an example, the input sensor ISU may further include transmission lines electrically connected to the other side of the first to tenth transmission electrodes TE1 to TE10.

The input sensor ISU is electrically connected to the readout circuit ROC (refer to FIG. 2) through the first to tenth transmission lines TL1 to TL10 and the first to fourteenth reception lines RL1 to RL14. The readout circuit ROC may control the operation of the input sensor ISU. In an embodiment, the readout circuit ROC may control the operation of the input sensor ISU in first to fourth operation modes.

In the first to fourth operation modes, the readout circuit ROC may transmit a transmission signal to the first to tenth transmission lines TL1 to TL10 and/or the first to fourteenth reception lines RL1 to RL14, and may receive a reception signal from the first to tenth transmission lines TL1 to TL10 and/or the first to fourteenth reception lines RL1 to RL14.

The operation of the readout circuit ROC and the operation of the input sensor ISU in each of the first to fourth operation modes will be described in more detail later.

Figure 7:
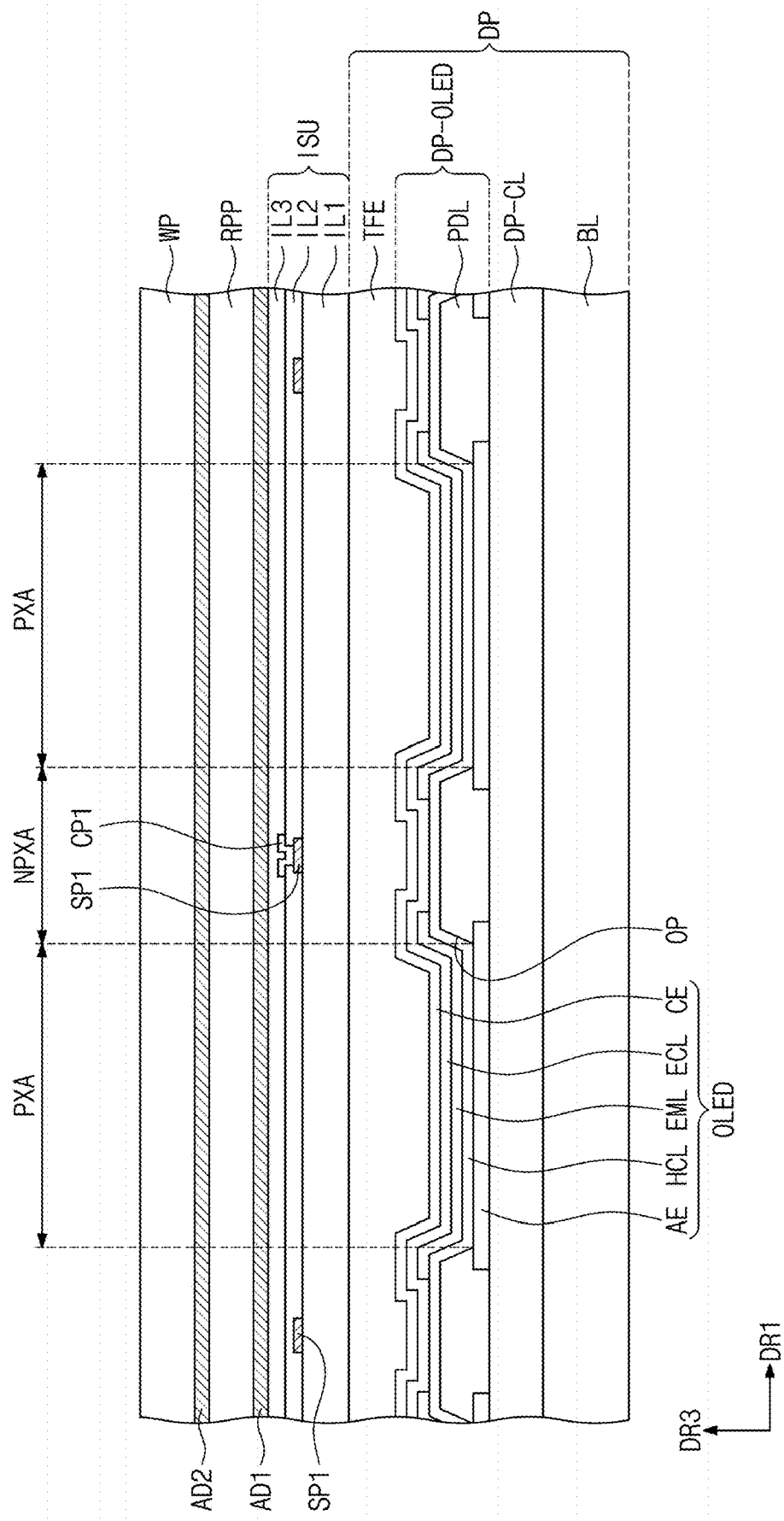
FIG. 7 is a cross-sectional view of a display device according to an embodiment.

FIG. 7 is a cross-sectional view of a display device according to an embodiment.

As illustrated in FIG. 7, a display panel DP includes a base layer BL, a circuit element layer DP-CL disposed on the base layer BL, a light emitting element layer DP-OLED, and a thin film encapsulation layer TFE. The display panel DP may further include functional layers, such as an anti-reflection layer and a refractive index control layer.

The base layer BL may include a synthetic resin film. A synthetic resin layer may be formed on a working substrate used in manufacturing the display panel DP. Thereafter, a conductive layer, an insulation layer, and/or the like may be formed on the synthetic resin layer. When the working substrate is removed, the synthetic resin layer corresponds to the base layer BL. The synthetic resin layer may be a polyimide-based resin layer, but the material thereof is not limited thereto. In addition, the base layer BL may include at least one of a glass substrate, a metal substrate, an organic/inorganic composite material substrate, and the like.

The circuit element layer DP-CL includes at least one insulation layer and at least one circuit element. Hereinafter, an insulation layer included in the circuit element layer DP-CL is referred to as an intermediate insulation layer. The intermediate insulation layer includes at least one intermediate inorganic film and at least one intermediate organic film. The circuit element includes a signal line and a driving circuit of a pixel, and/or the like. The circuit element layer DP-CL may be formed through a forming process of an insulation layer, a semiconductor layer, and a conductive layer by coating, deposition, and/or the like, and a patterning process of an insulation layer, a semiconductor layer, and a conductive layer by a photolithography process.

The light emitting element layer DP-OLED may include a pixel definition film (or layer) PDL and an organic light emitting diode OLED. The pixel definition film PDL may include an organic material. On the circuit element layer DP-CL, a first electrode AE is disposed. Over the first electrode AE, the pixel definition film PDL is formed. The pixel definition film PDL may include an opening OP. The opening OP of the pixel definition film PDL exposes at least a portion of the first electrode AE. In an embodiment, the pixel definition film PDL may be omitted.

A hole control layer HCL may be disposed on the first electrode AE. On the hole control layer HCL, a light emitting layer EML is disposed. The light emitting layer EML may be disposed in a region corresponding to the opening OP. For instance, the light emitting layer EML may be divided and formed in each of the pixels PX (refer to FIG. 5). The light emitting layer EML may include an organic material and/or an inorganic material. The light emitting layer EML may generate a predetermined color of light.

On the light emitting layer EML, an electron control layer ECL is disposed. On the electron control layer ECL, the second electrode CE is disposed. The second electrode CE is commonly disposed in the pixels PX.

On the second electrode CE, the thin film encapsulation layer TFE is disposed. The thin film encapsulation layer TFE encapsulates the light emitting element layer DP-OLED. The thin film encapsulation layer TFE includes at least one insulation layer. The thin film encapsulation layer TFE according to an embodiment may include at least one inorganic film (hereinafter, an encapsulation inorganic film). The thin film encapsulation layer TFE according to an embodiment may include at least one organic film (hereinafter, an encapsulation organic film) and at least one encapsulation inorganic film.

The encapsulation inorganic film protects the light emitting element layer DP-OLED from moisture/oxygen, and the encapsulation organic film protects the light emitting element layer DP-OLED from foreign materials, such as dust particles. The encapsulation inorganic film may include at least one of a silicon nitride layer, a silicon oxynitride layer, a silicon oxide layer, a titanium oxide layer, and an aluminum oxide layer, and/or the like, but embodiments are not limited thereto. The encapsulation organic film may include an acrylic organic film, but embodiments are not limited thereto.

The input sensor ISU includes a base layer IL1 first and second conductive layers disposed thereon, and first and second insulation layers IL2 and IL3. The base layer IL1 may include an inorganic substance (or material), and may include, for example, a silicon nitride layer. An inorganic film disposed on the uppermost side of the thin film encapsulation layer TFE may also include silicon nitride. The silicon nitride layer of the thin film encapsulation layer TFE and the base layer IL1 may be formed under different deposition conditions.

The first conductive layer is disposed on the base layer IL1. The first conductive layer may include a first sensing pattern SP1, a second sensing pattern SP2, and a second connecting pattern CP2. The second conductive layer is disposed on the first conductive layer. The second conductive layer may include a first connecting pattern CP1. The first insulation layer IL2 is disposed between the first conductive layer and the second conductive layer. The first insulation layer IL2 allows the first conductive layer and the second conductive layer to be spaced apart and separated from each other on a cross section. On the first insulation layer IL2, a contact hole to partially expose the first sensing pattern SP1 is provided, and through the contact hole, the first connecting pattern CP1 may be connected to the first sensing pattern SP1. The second insulation layer IL3 is disposed on the first insulation layer IL2. The second insulation layer IL3 may cover the first insulation layer IL2. The second insulation layer IL3 protects the first insulation layer IL2 from an external environment.

Mesh lines of the first sensing pattern SP1 and of the second sensing pattern SP2 may define a plurality of mesh holes. The mesh lines may have a three-layered structure of titanium/aluminum/titanium, but embodiments are not limited thereto.

In an embodiment, the input sensor ISU may be directly disposed on the display panel DP. In this disclosure, "being directly disposed" means that there is no adhesive film disposed between the input sensor ISU and the display panel DP. For example, the input sensor ISU may be formed on the display panel DP through a series of processes. In this case, the input sensor ISU may be referred to as an input sensing layer.

A portion in which the first electrode AE and the light emitting layer EML are disposed may be referred to as a pixel region PXA. A plurality of pixel regions PXA corresponding to the plurality of pixels PX may be disposed spaced apart from each other in the first direction DR1 and in the second direction DR2 (refer to FIG. 5). A non-pixel region NPAX is disposed between pixel regions PXA, and may surround the pixel region PXA.

On an upper surface of the input sensor ISU, the anti-reflector RPP may be disposed. As an example, the anti-reflector RPP may include a polarizing film. The anti-reflector RPP may further include at least one of a protective film and other functional films in addition to the polarizing film, but hereinafter, only a polarizing film is illustrated for convenience of description. Between the anti-reflector RPP and the input sensor ISU, the adhesive member AD1 may be disposed. Accordingly, the anti-reflector RPP may be boned to the input sensor ISU by the adhesive member AD1. The window WP may be coupled onto the anti-reflector RPP through the adhesive member AD2.

Referring to FIG. 6, the input sensor ISU may be a capacitance type touch sensor. In an embodiment, the first to tenth transmission electrodes TE1 to TE10 receive a transmission signal and the first to fourteenth reception electrodes RE1 to RE14 output the amount of change in capacitance between the first to tenth transmission electrodes TE1 to TE10 and the first to fourteenth reception electrodes RE1 to RE14. When a first transmission electrode TE1 receives a transmission signal (or a driving signal), the first transmission electrode TE1 is capacitively coupled to the first to fourteenth reception electrodes RE1 to RE14. When a part of a user's body is positioned on a specific reception electrode among the first to fourteenth reception electrodes RE1 to RE14 capacitively coupled, for example, the first reception electrode RE1, the capacitance between the first transmission electrode TE1 and the first reception electrode RE1 is changed. The readout circuit ROC (refer to FIG. 2) may calculate the coordinate information of the position of a user's touch by detecting the changed capacitance of a sensing signal received from a first reception line RL1 connected to the first reception electrode RE1. In an embodiment, the first to fourteenth reception electrodes RE1 to RE14 receive a transmission signal and the first to tenth transmission electrodes TE1 to TE10 output the amount of change in capacitance between the first to tenth transmission electrodes TE1 to TE10 and the first to fourteenth reception electrodes RE1 to RE14.

Figure 8:
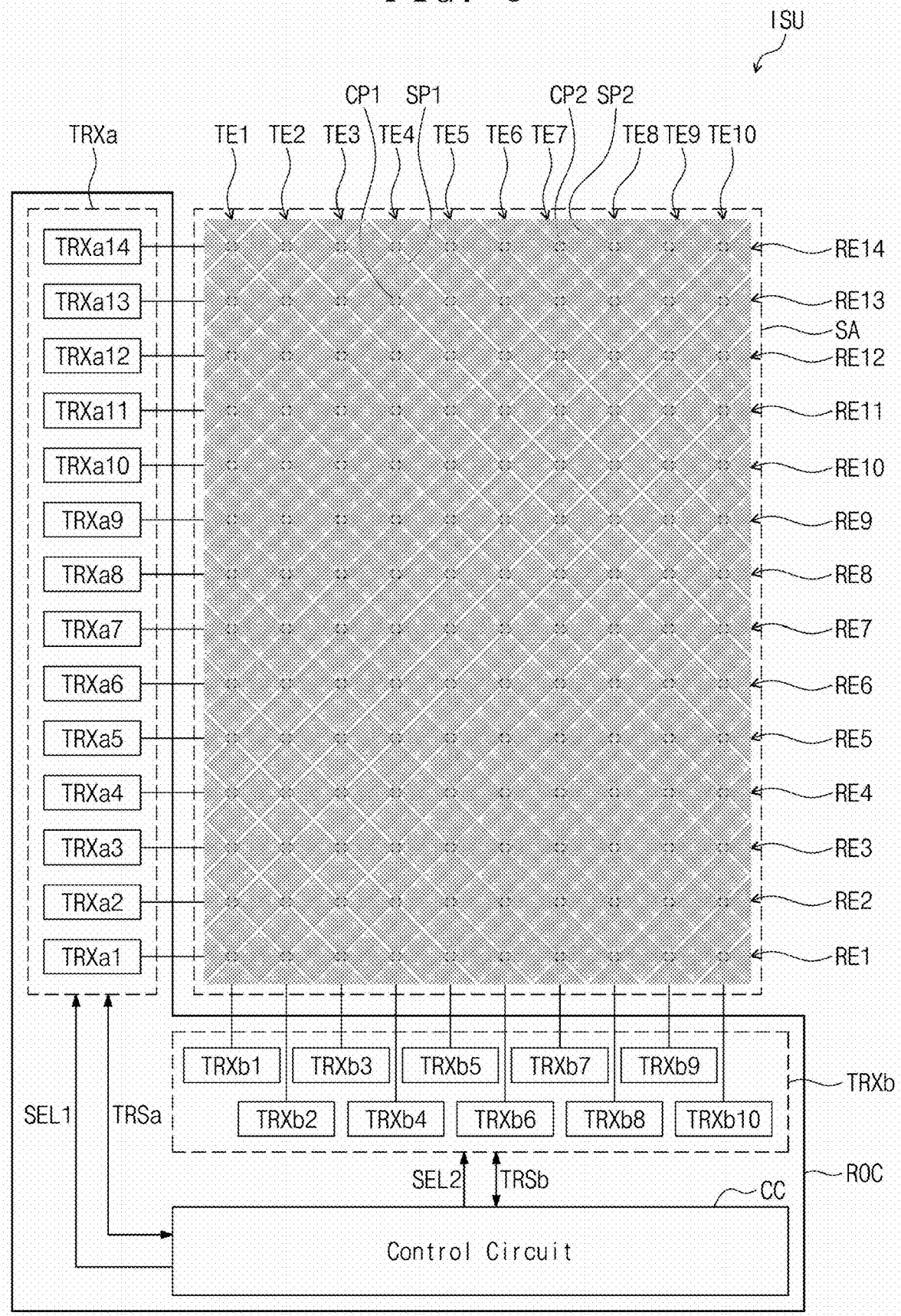
FIG. 8 is a block diagram showing a configuration of a readout circuit according to an embodiment.

FIG. 8 is a block diagram showing a configuration of the readout circuit ROC according to an embodiment.

Referring to FIG. 8, the readout circuit ROC may include a first transmission/reception circuit TRXa, a second transmission/reception circuit TRXb, and a control circuit CC. The readout circuit ROC may further include a voltage generator that generates voltages for the operation of the first transmission/reception circuit TRXa, the second transmission/reception circuit TRXb, and the control circuit CC.

The first transmission/reception circuit TRXa includes first transceivers TRXa1 to TRXa14 respectively corresponding to the first to fourteenth reception electrodes RE1 to RE14. Each of the first transceivers TRXa1 to TRXa14 may be electrically connected to a corresponding reception electrode among the first to fourteenth reception electrodes RE1 to RE14.

The second transmission/reception circuit TRXb includes second transceivers TRXb1 to TRXb10 respectively corresponding to the first to tenth transmission electrodes TE1 to TE10. Each of the second transceivers TRXb1 to TRXb10 may be electrically connected to a corresponding transmission electrode among the first to tenth transmission electrodes TE1 to TE10.

The control circuit CC may control the first transmission/reception circuit TRXa and the second transmission/reception circuit TRXb. The control circuit CC may output a first selection signal SEL1 to control the operation of the first transmission/reception circuit TRXa, and may output a second selection signal SEL2 to control the operation of the second transmission/reception circuit TRXb.

The control circuit CC may transmit/receive a first transmission/reception signal TRSa to/from the first transmission/reception circuit TRXa. The control circuit CC may transmit/receive a second transmission/reception signal TRSb to/from the second transmission/reception circuit TRXb.

Figure 9:
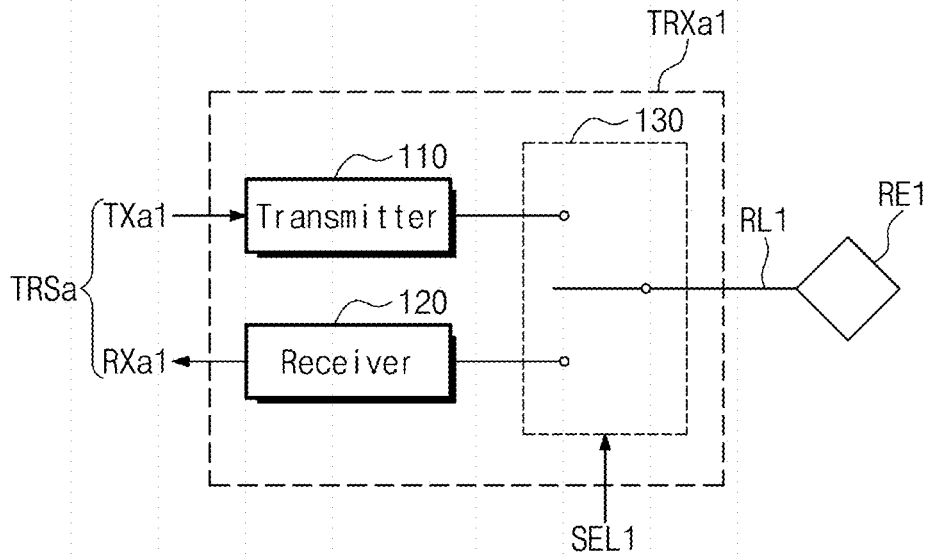
FIG. 9 is a view showing a first transceiver according to an embodiment.

FIG. 9 is a view showing a first transceiver TRXa1 according to an embodiment.

FIG. 9 illustrates the first transceiver TRXa1 among the first transceivers TRXa1 to TRXa14 in the first transmission/reception circuit TRXa illustrated in FIG. 8. First transceivers TRXa2 to TRXa14 may also include the same components as the first transceiver TRXa1.

As illustrated in FIGS. 8 and 9, the first transceiver TRXa1 receives the first selection signal SEL1 from the control circuit CC. The first transceiver TRXa1 may transmit/receive the first transmission/reception signal TRSa to/from the control circuit CC. The first transmission/reception signal TRSa may be any one of a first transmission signal TXa1 and a first reception signal RXa1.

The first transceiver TRXa1 includes a transmitter 110, a receiver 120, and a switch 130.

In response to the first selection signal SEL1 from the control circuit CC, the switch 130 electrically connects the first reception line RL1 to any one of the transmitter 110 and the receiver 120.

The transmitter 110 transmits the first transmission signal TXa1 from the control circuit CC to the first reception electrode RE1 through the switch 130 and the first reception line RL1. The transmitter 110 may convert the first transmission signal TXa1 from the control circuit CC to a voltage level suitable for the first reception electrode RE1.

The receiver 120 receives a signal from the first reception electrode RE1 through the first reception line RL1 and the switch 130, and transfers the first reception signal RXa1 to the control circuit CC. The signal received from the first reception electrode RE1 through the first reception line RL1 and the switch 130 by the receiver 120 may be an analog capacitance signal associated with the user input TC (refer to FIG. 1). The receiver 120 may convert the analog capacitance signal into the first reception signal RXa1, which may be a digital signal.

Figure 10:
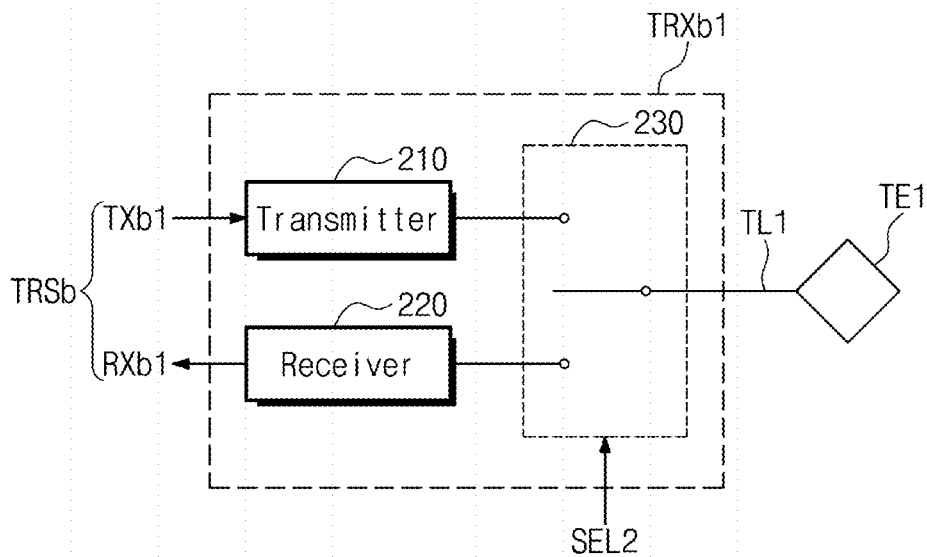
FIG. 10 is a view showing a second transceiver according to an embodiment.

FIG. 10 is a view showing a second transceiver TRXb1 according to an embodiment.

FIG. 10 illustrates the second transceiver TRXb1 among the second transceivers TRXb1 to TRXb10 in the second transmission/reception circuit TRXb illustrated in FIG. 8. Second transceivers TRXb2 to TRXb10 may also include the same components as the second transceiver TRXb1.

As illustrated in FIGS. 8 and 10, the second transceiver TRXb1 receives the second selection signal SEL2 from the control circuit CC. The second transceiver TRXb1 may transmit/receive the second transmission/reception signal TRSb to/from the control circuit CC. The second transmission/reception signal TRSb may be any one of a second transmission signal TXb1 and a second reception signal RXb1.

The second transceiver TRXb1 includes a transmitter 210, a receiver 220, and a switch 230.

In response to the second selection signal SEL2 from the control circuit CC, the switch 230 electrically connects the first transmission line TL1 to any one of the transmitter 210 and the receiver 220.

The transmitter 210 transmits the second transmission signal TXb1 from the control circuit CC to the first transmission electrode TE1 through the switch 230 and a first transmission line TL1. The transmitter 210 may convert the second transmission signal TXb1 from the control circuit CC to a voltage level suitable for the first transmission electrode TE1.

The receiver 220 receives a signal from the first transmission electrode TE1 through the first transmission line TL1 and the switch 230, and transfers the second reception signal RXb1 to the control circuit CC. The signal received from the first transmission electrode TE1 through the first transmission line TL1 and the switch 230 by the receiver 220 may be an analog capacitance signal associated with the user input TC (refer to FIG. 1). The receiver 220 may convert the analog capacitance signal into the second reception signal RXb1, which may be a digital signal.

Referring to FIGS. 8, 9, and 10, the first transmission/reception circuit TRXa and the second transmission/reception circuit TRXb may operate in any one of the first to fourth operation modes in response to the first selection signal SEL1 and the second selection signal SEL2 from the control circuit CC.

The following Table 1 illustratively shows the first to fourth operation modes according to the first selection signal SEL1 and the second selection signal SEL2.

TABLE 1

| First selection signal (SEL1) | Second selection signal (SEL2) | Operation mode |
| --- | --- | --- |
| 0 | 0 | First operation mode |
| 1 | 1 | Second operation mode |
| 0 | 1 | Third operation mode |
| 1 | 0 | Fourth operation mode |

The first to fourth operation modes according to the first selection signal SEL1 and the second selection signal SEL2 are merely illustrative for the description, and as such, embodiments are not limited thereto.

FIGS. 11A to 11D are views showing an operation of the first transceiver TRXa1 and the second transceiver TRXb1 according to the first to fourth operation modes according to various embodiments.

Figure 11A:
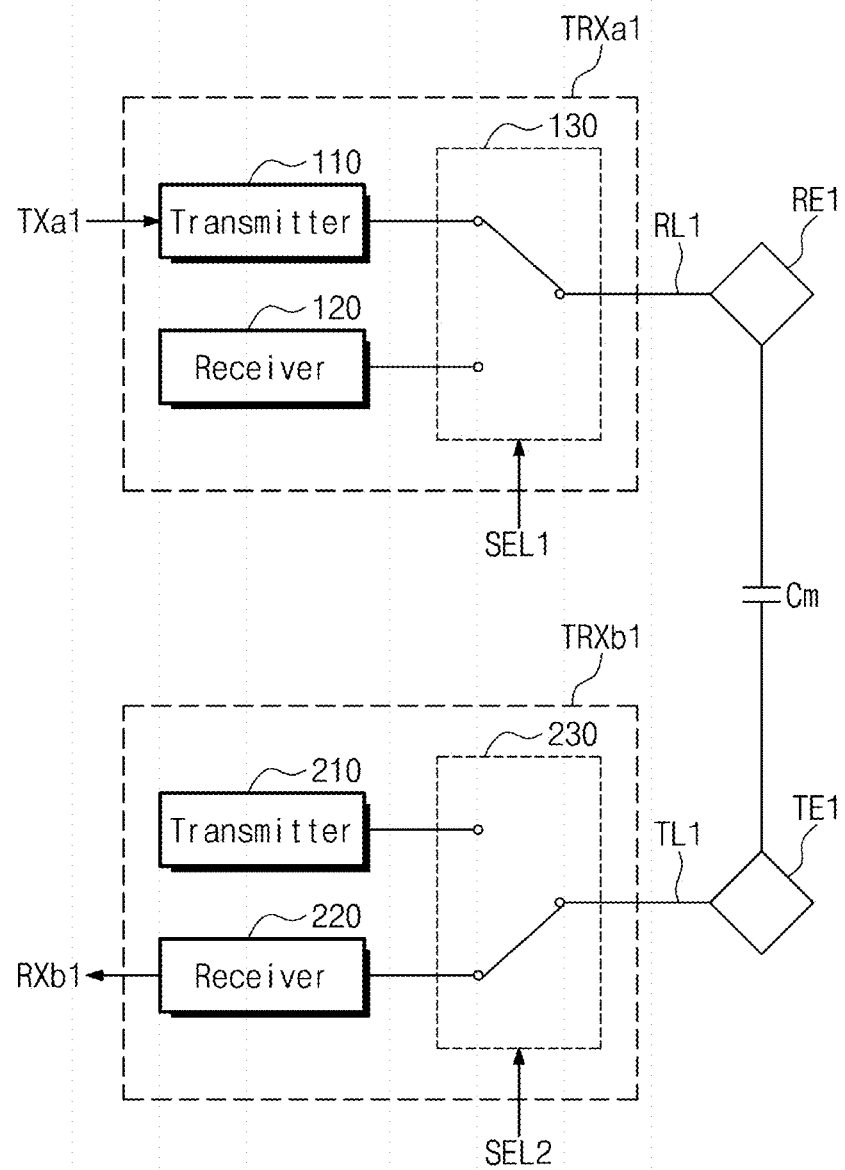
FIGS. 11A, 11B, 11C, and 11D are views illustratively showing an operation of a first transceiver and a second transceiver according to first to fourth operation modes according to various embodiments.

Referring to FIGS. 8 and 11A, when the first selection signal SEL1 has a first value (for example, "0" or a low level) and the second selection signal SEL2 has the first value (for example, "0" or a low level), the first transceiver TRXa1 and the second transceiver TRXb1 may operate in a first operation mode.

During the first operation mode, the operation of the first transceiver TRXa1 and the operation of the second transceiver TRXb1 are as follows.

In response to the first selection signal SEL1 from the control circuit CC, the switch 130 in the first transceiver TRXa1 electrically connects the first reception line RL1 to the transmitter 110. The transmitter 110 in the first transceiver TRXa1 may transmit the first transmission signal TXa1 from the control circuit CC to the first reception electrode RE1 through the first reception line RL1.

In response to the second selection signal SEL2 from the control circuit CC, the switch 230 in the second transceiver TRXb1 electrically connects the first transmission line TL1 to the receiver 220.

A capacitance Cm between the first reception electrode RE1 and the first transmission electrode TE1 may be transferred to the receiver 220 through the first transmission line TL1 and the switch 230. The receiver 220 receives a signal from the first transmission electrode TE1, and transfers the second reception signal RXb1 to the control circuit CC.

Figure 11B:
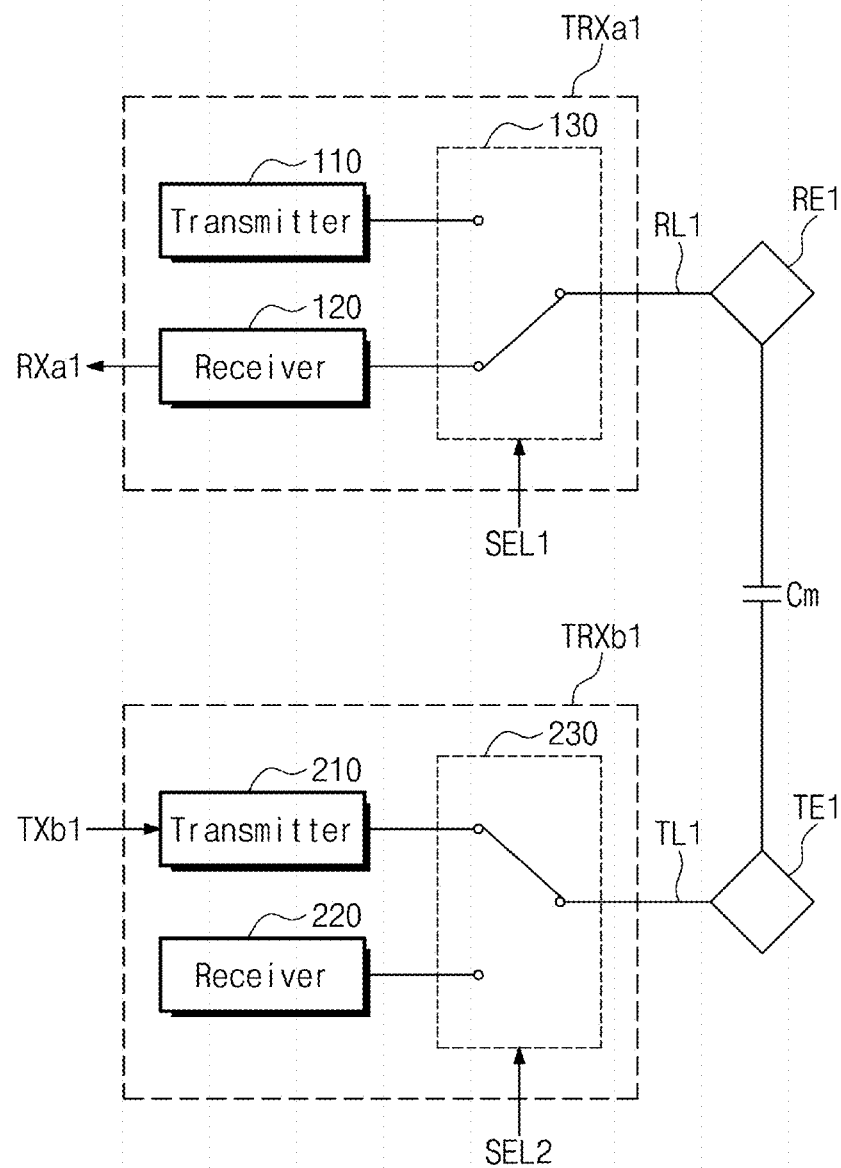

Referring to FIGS. 8 and 11B, when the first selection signal SEL1 has a second value (for example, "1" or a high level) and the second selection signal SEL2 has a second value (for example, "1" or a high level), the first transceiver TRXa1 and the second transceiver TRXb1 may operate in a second operation mode.

During the second operation mode, the operation of the first transceiver TRXa1 and the operation of the second transceiver TRXb1 are as follows.

In response to the first selection signal SEL1 from the control circuit CC, the switch 130 in the first transceiver TRXa1 electrically connects the first reception line RL1 to the receiver 120.

In response to the second selection signal SEL2 from the control circuit CC, the switch 230 in the second transceiver TRXb1 electrically connects the first transmission line TL1 to the transmitter 210. The transmitter 210 in the second transceiver TRXb1 may transmit the second transmission signal TXb1 from the control circuit CC to the first transmission electrode TE1 through the first transmission line TL1.

The capacitance Cm between the first reception electrode RE1 and the first transmission electrode TE1 may be transferred to the receiver 120 through the first reception line RL1 and the switch 130. The receiver 120 receives a signal from the first reception electrode RE1, and transfers the first reception signal RXa1 to the control circuit CC.

Figure 11C:
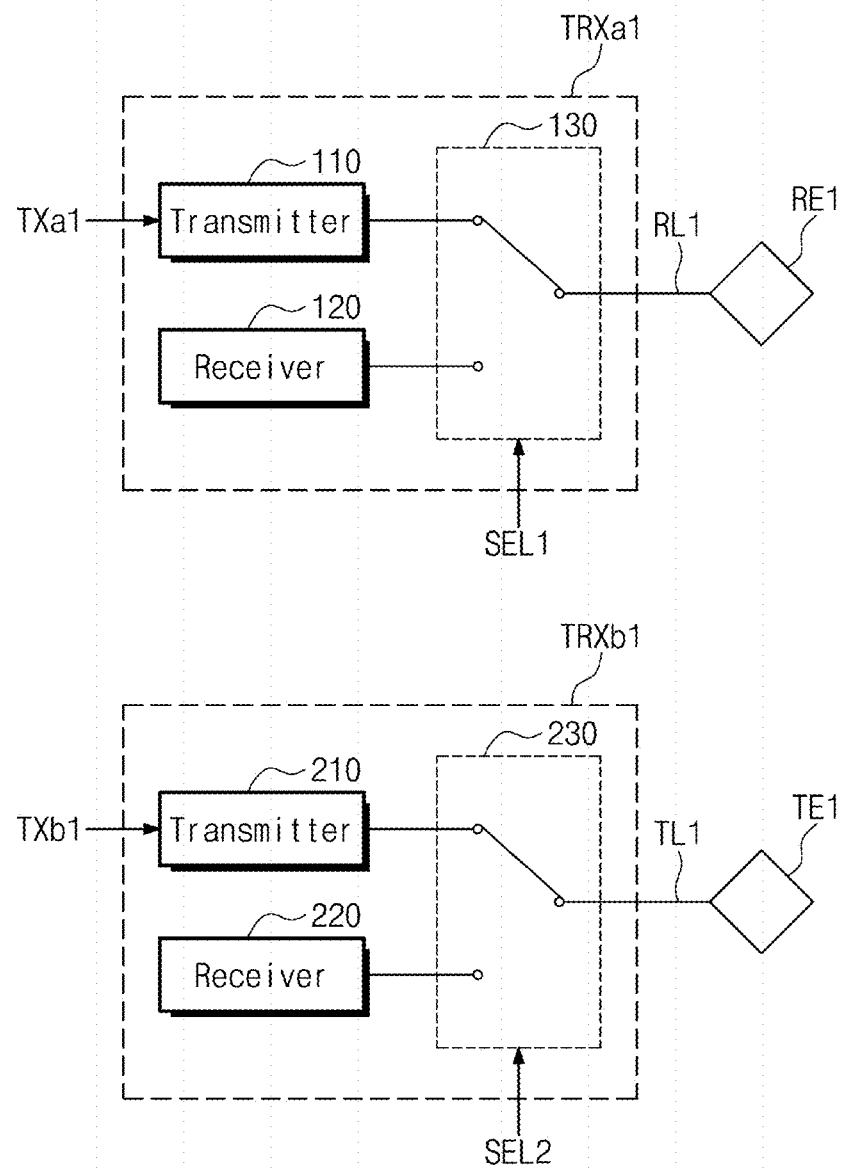

Referring to FIGS. 8 and 11C, when the first selection signal SEL1 has the first value (for example, "0" or a low level) and the second selection signal SEL2 has the second value (for example, "1" or a high level), the first transceiver TRXa1 and the second transceiver TRXb1 may operate in a third operation mode.

During the third operation mode, the operation of the first transceiver TRXa1 and the operation of the second transceiver TRXb1 are as follows.

In response to the first selection signal SEL1 from the control circuit CC, the switch 130 in the first transceiver TRXa1 electrically connects the first reception line RL1 to the transmitter 110. The transmitter 110 in the first transceiver TRXa1 may transmit the first transmission signal TXa1 from the control circuit CC to the first reception electrode RE1 through the first reception line RL1.

In response to the second selection signal SEL2 from the control circuit CC, the switch 230 in the second transceiver TRXb1 electrically connects the first transmission line TL1 to the transmitter 210. The transmitter 210 in the second transceiver TRXb1 may transmit the second transmission signal TXb1 from the control circuit CC to the first transmission electrode TE1 through the first transmission line TL1.

In the third operation mode, the first reception line RL1 may be electrically connected to the transmitter 110 in the first transceiver TRXa1, and the first transmission line TL1 may be electrically connected to the transmitter 210 in the second transceiver TRXb1.

The input sensor ISU (refer to FIG. 6) may sense an input from the electronic pen PEN (refer to FIG. 1). The third operation mode may be a mode in which the first transmission signal TXa1 and the second transmission signal TXb1 from the control circuit CC are transferred to the first reception electrode RE1 and the first transmission electrode TE1. The first transmission signal TXa1 and the second transmission signal TXb1 may be uplink signals to be transmitted to the electronic pen PEN.

Figure 11D:
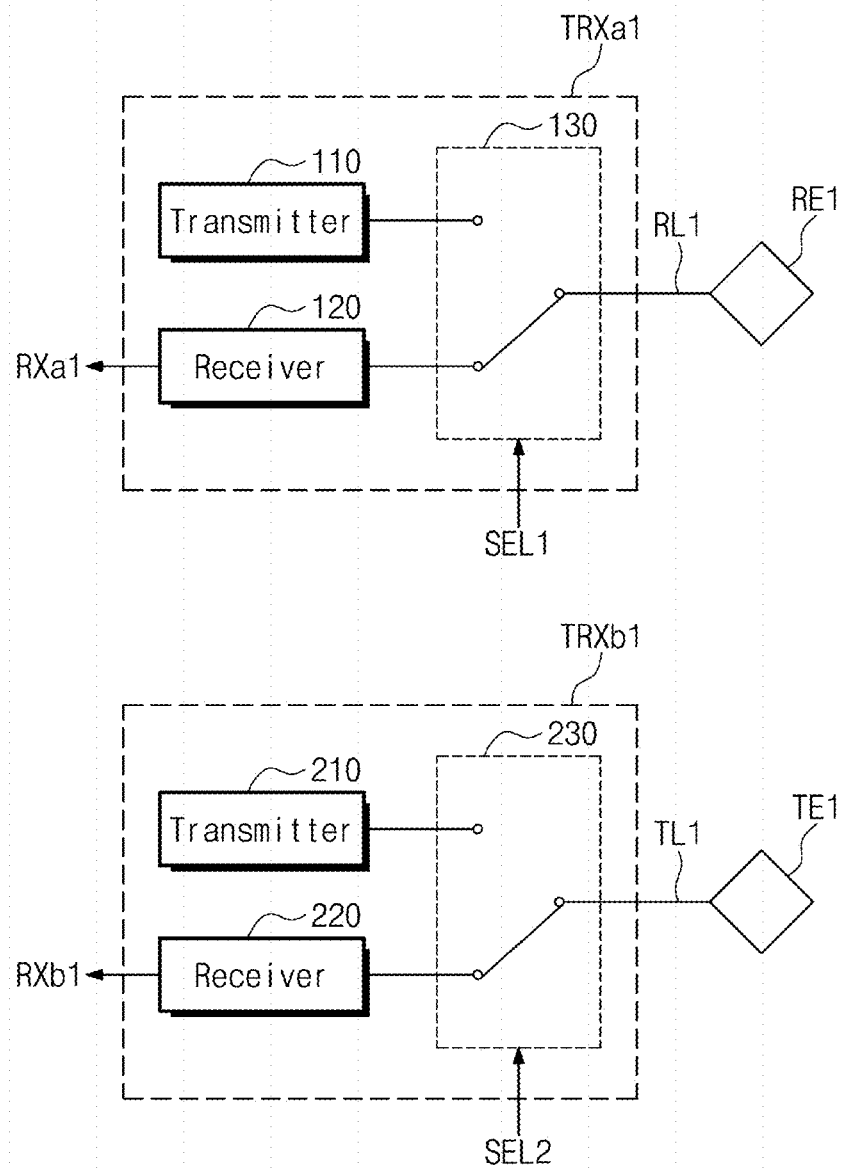

Referring to FIGS. 8 and 11D, when the first selection signal SEL1 has the second value (for example, "1" or a high level) and the second selection signal SEL2 has the first value (for example, "0" or a low level), the first transceiver TRXa1 and the second transceiver TRXb1 may operate in a fourth operation mode.

During the fourth operation mode, the operation of the first transceiver TRXa1 and the operation of the second transceiver TRXb1 are as follows.

In response to the first selection signal SEL1 from the control circuit CC, the switch 130 in the first transceiver TRXa1 electrically connects the first reception line RL1 to the receiver 120. The receiver 120 receives a signal from the first reception electrode RE1, and transfers the first reception signal RXa1 to the control circuit CC.

In response to the second selection signal SEL2 from the control circuit CC, the switch 230 in the second transceiver TRXb1 electrically connects the first transmission line TL1 to the receiver 220. The receiver 220 receives a signal from the first transmission electrode TE1, and transfers the second reception signal RXb1 to the control circuit CC.

In the fourth operation mode, the first reception line RL1 may be electrically connected to the receiver 120 in the first transceiver TRXa1, and the first transmission line TL1 may be electrically connected to the receiver 220 in the second transceiver TRXb1.

The input sensor ISU (refer to FIG. 6) may sense an input from the electronic pen PEN (refer to FIG. 1). The fourth operation mode may be a mode in which the first reception signal RXa1 and the second reception signal RXb1 from the first reception electrode RE1 and the first transmission electrode TE1 are transmitted to the control circuit CC. The first reception signal RXa1 and the second reception signal RXb1 may be downlink signals to be received from the electronic pen PEN.

FIGS. 12A to 12D are timing diagrams showing first transmission signals, second transmission signals, first reception signals, and second reception signals in first to fourth operation modes according to various embodiments.

First, FIG. 12A is a timing diagram showing first transmission signals TXa1 to TXa14 and second reception signals RXb1 to RXb10 in the first operation mode according to an embodiment.

Referring to FIGS. 8, 11A, and 12A, the first transmission signals TXa1 to TXa14 from the control circuit CC may be sequentially provided to the reception electrodes RE1 to RE14 in the first operation mode. A capacitance Cm between the reception electrodes RE1 to RE14 and the transmission electrodes TE1 to TE10 may be transferred to the control circuit CC as the second reception signals RXb1 to RXb10.

FIG. 12B is a timing diagram showing first reception signals RXa1 to RXa14 and second transmission signals TXb1 to TXb10 in the second operation mode according to an embodiment.

Referring to FIGS. 8, 11B, and 12B, the second transmission signals TXb1 to TXb10 from the control circuit CC may be sequentially provided to the transmission electrodes TE1 to TE10 in the second operation mode. A capacitance Cm between the transmission electrodes TE1 to TE10 and the reception electrodes RE1 to RE14 may be transferred to the control circuit CC as the first reception signals RXa1 to RXa14.

Figure 12C:
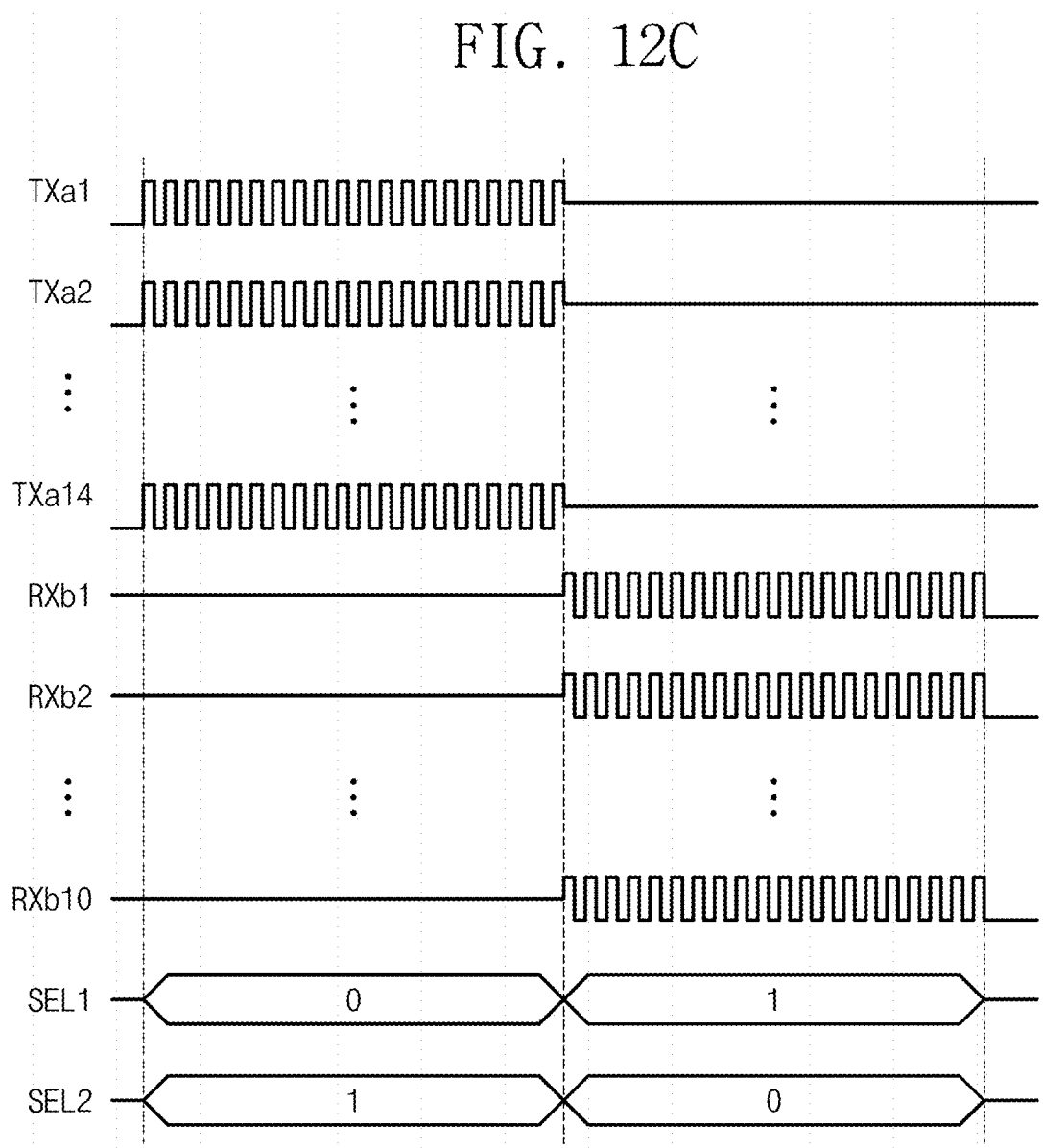

FIG. 12C is a timing diagram showing the first transmission signals TXa1 to TXa14 and the second reception signals RXb1 to RXb10 in the third operation mode.

Referring to FIGS. 8, 11C, and 12C, the first transmission signals TXa1 to TXa14 from the control circuit CC may be provided to the reception electrodes RE1 to RE14 in the third operation mode. At this time, the second reception signals RXb1 to RXb10 may be in a floating state. In another embodiment, the second reception signals RXb1 to RXb10 may be at a ground voltage level in the third operation mode.

Referring to FIGS. 8, 11D, and 12C, the second reception signals RXb1 to RXb10 may be provided to the control circuit CC from the transmission electrodes TE1 to TE10 in the fourth operation mode. At this time, the first transmission signals TXa1 to TXa14 may be in a floating state. In another embodiment, the first transmission signals TXa1 to TXa14 may be at a ground voltage level in the fourth operation mode.

Figure 12D:
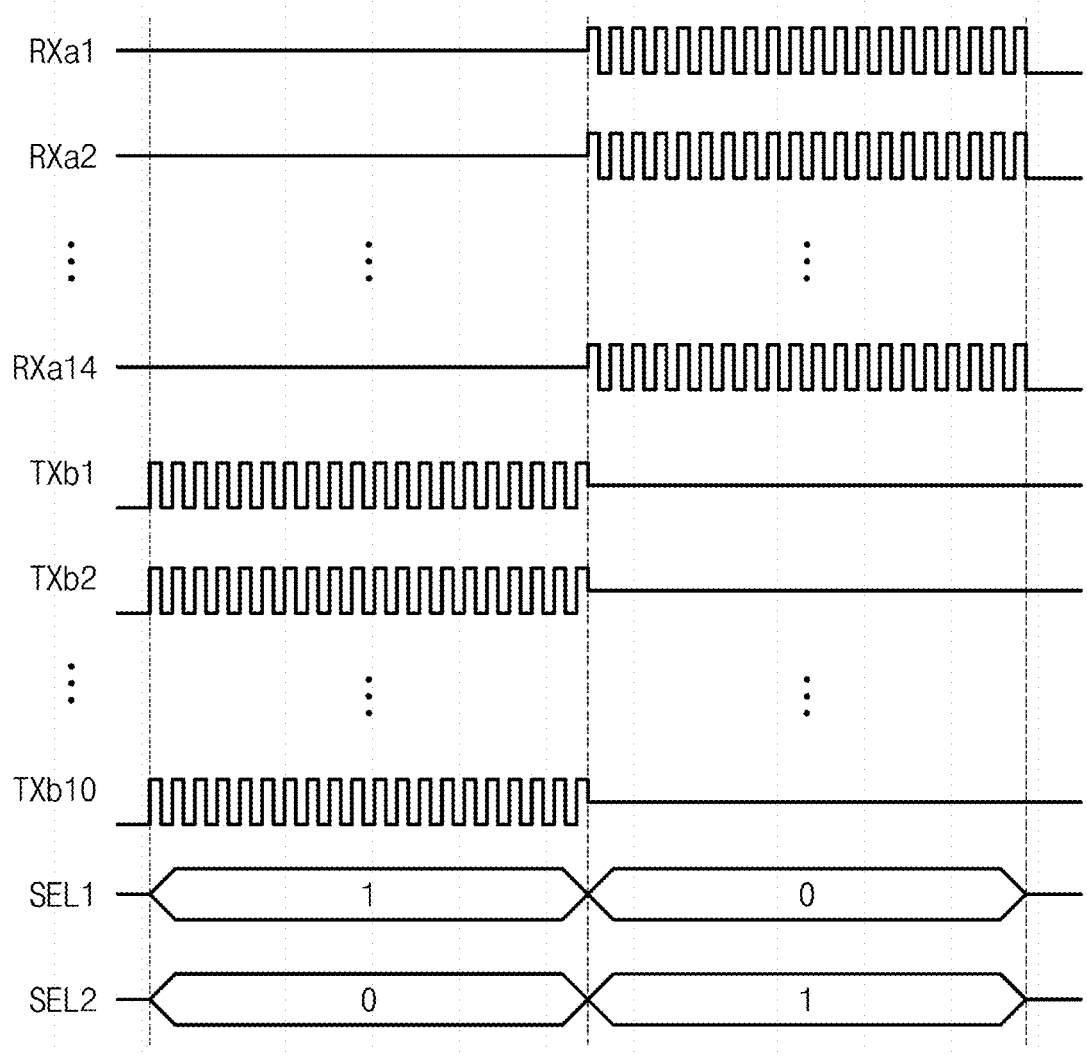

FIG. 12D is a timing diagram showing the first reception signals RXa1 to RXa14 and the second transmission signals TXb1 to TXb10 in the fourth operation mode according to an embodiment.

Referring to FIGS. 8, 11C, and 12D, the second transmission signals TXb1 to TXb10 from the control circuit CC may be provided to the transmission electrodes TE1 to TE10 in the third operation mode. At this time, the first reception signals RXa1 to RXa14 may be in a floating state. In another embodiment, the first reception signals RXa1 to RXa14 may be at a ground voltage level in the third operation mode.

Referring to FIGS. 8, 11D, and 12D, the first reception signals RXa1 to RXa14 may be provided to the control circuit CC from the reception electrodes RE1 to RE14 in the fourth operation mode. At this time, the second transmission signals TXb1 to TXb10 may be in a floating state. In another embodiment, the second transmission signals TXb1 to TXb10 may be at a ground voltage level in the fourth operation mode.

Figure 13:
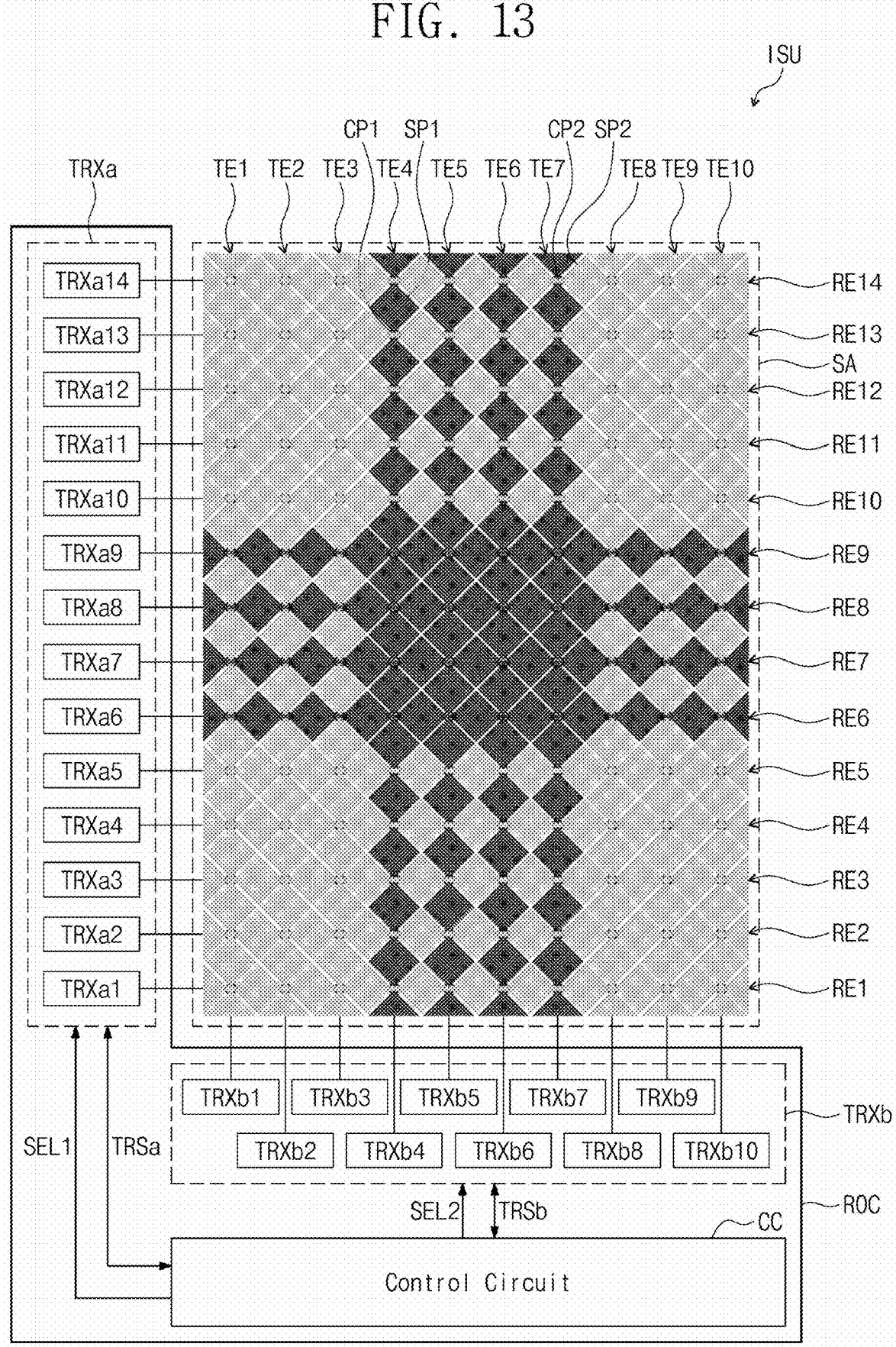
FIG. 13 is a view showing an example of an input sensor operating in a fifth operation mode according to an embodiment.
Figure 14:
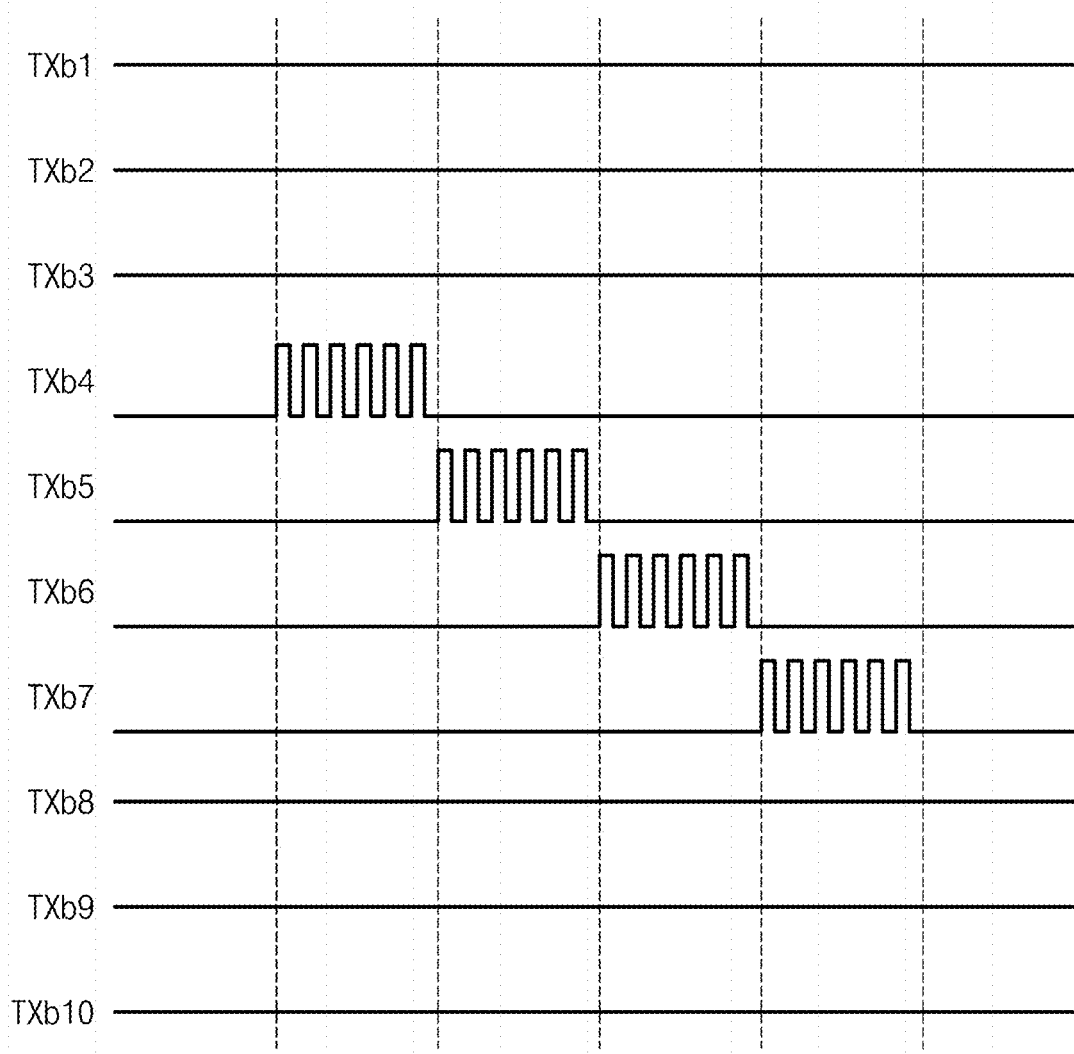
FIG. 14 is a timing diagram showing second transmission signals provided to first to tenth transmission lines of the input sensor illustrated in FIG. 13 according to an embodiment.
Figure 15:
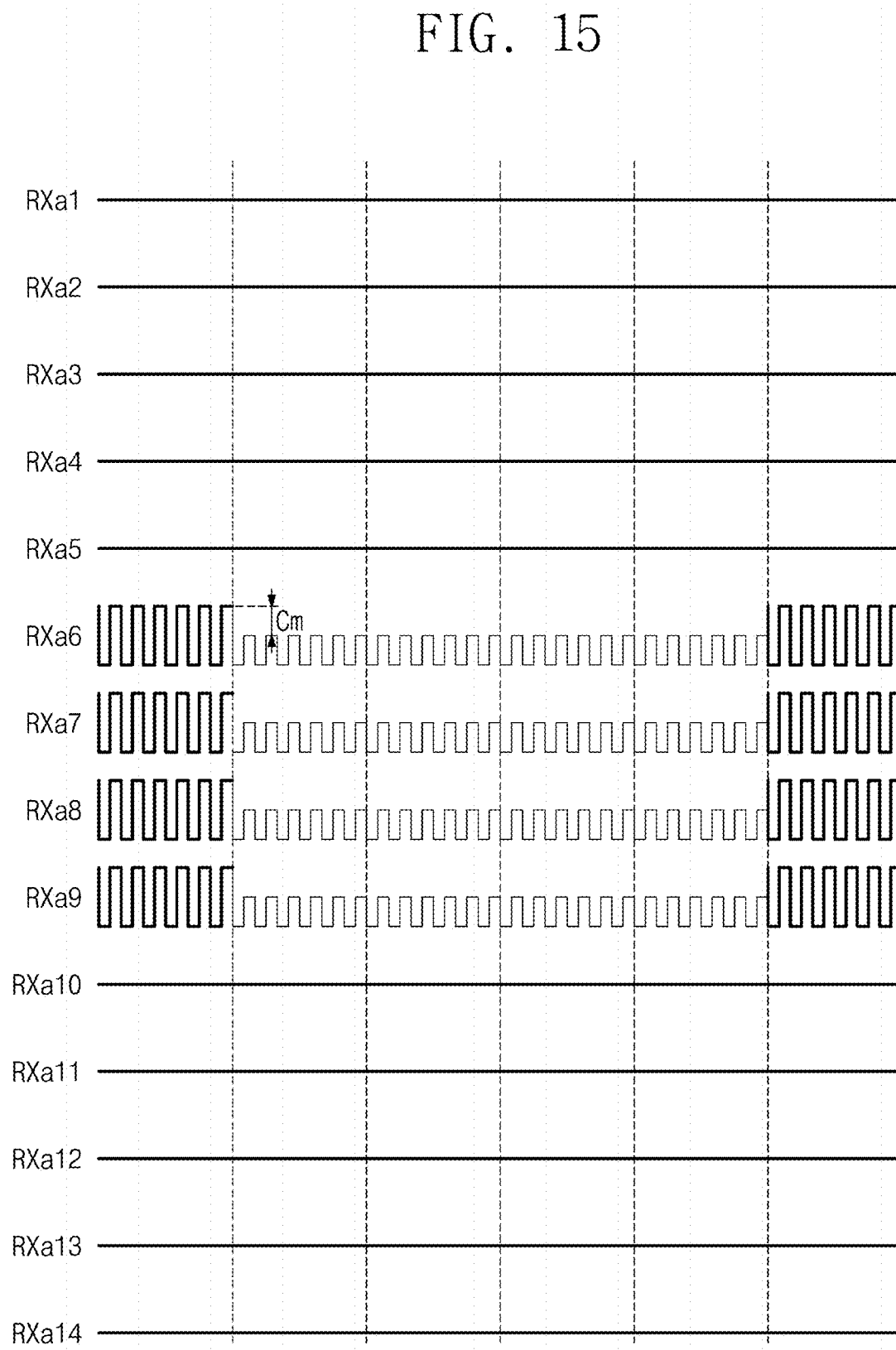
FIG. 15 is a timing diagram showing first reception signals provided to first to fourteenth reception lines of the input sensor illustrated in FIG. 13 according to an embodiment.

FIG. 13 is a view showing an example of the input sensor ISU operating in a fifth operation mode according to an embodiment. FIG. 14 is a timing diagram showing the second transmission signals TXb1 to TXb10 provided to the first to tenth transmission lines TL1 to TL10 of the input sensor ISU illustrated in FIG. 13 according to an embodiment. FIG. 15 is a timing diagram showing first reception signals RXa1 to RXa14 provided to the first to fourteenth reception lines RL1 to RL14 of the input sensor ISU illustrated in FIG. 13 according to an embodiment.

Referring to FIGS. 13 to 15, in a specific application program or in a specific situation, it may be desired to sense an input for a partial region, rather than the entire region, of the input sensor ISU. For example, it may be desired to sense an input for a region in which fourth to seventh transmission electrodes TE4 to TE7 and sixth to ninth reception electrodes RE6 to RE9 intersect. In the fifth operation mode, the control circuit CC sequentially outputs second transmission signals TXb4 to TXb7 to the fourth to seventh transmission electrodes TE4 to TE7, and receives first reception signals RXa6 to RXa9 from the sixth to ninth reception electrodes RE6 to RE9. At this time, second transmission signals TXb1 to TXb3 and TXb8 to TXb10 and first reception signals RXa1 to RXa5 and RXa10 to RXa14 may be in a floating state.

To transfer the second transmission signals TXb4 to TXb7 from the control circuit CC to the fourth to seventh transmission electrodes TE4 to TE7, the switch 230 of each of second transceivers TRXb4 to TRXb7 electrically connects the transmitter 210 and a the fourth to seventh transmission electrodes TE4 to TE7 as illustrated in FIG. 11B. In addition, to transfer the first reception signals RXa6 to RXa9 from the sixth to ninth reception electrodes RE6 to RE9 to the control circuit CC, the switch 130 of each of first transceivers TRXa6 to TRXa9 electrically connects the receiver 120 and the sixth to ninth reception electrodes RE6 to RE9. Accordingly, it is possible to sense an input for a partial region of the input sensor ISU, and thereby, not for the entire region thereof.

The voltage (or current) of the first reception signals RXa6 to RXa9 may vary according to the capacitance Cm between the fourth to seventh transmission electrodes TE4 to TE7 and the sixth to ninth reception electrodes RE6 to RE9.

The display device DD (refer to FIG. 1) may have a function to measure and analyze the body composition of a user. The display device DD may obtain information on the body composition of the user utilizing the input sensor ISU. A fifth operation mode may be a mode in which the input sensor ISU operates to obtain the information on the body composition of the user. As an example, the body composition may include muscle mass, body fat mass, a moisture level, and/or the like.

The fifth operation mode may be a body composition measurement mode for measuring the skin moisture level of a user. When the user's skin comes in direct contact with the display surface DD-IS (refer to FIG. 1) of the display device DD, there is a change in capacitance due to the difference in dielectric constant between the moisture in the skin and air. The display device DD may measure the amount of moisture in the skin by sensing the change in capacitance.

To measure the moisture level of a user's skin, the contact between the user's skin and the display surface DD-IS is utilized, and the contact area may be more than half of the display surface DD-IS. When the contact area of the user's skin and the display surface DD-IS becomes larger, the capacitance between the first to tenth transmission electrodes TE1 to TE10 and the first to fourteenth reception electrodes RE1 to RE14 may be accumulated, so that a noise component may be included in a reception signal.

As illustrated in FIGS. 13 to 15, when only some transmission electrodes and some reception electrodes of the input sensor ISU, for example, the fourth to seventh transmission electrodes TE4 to TE7 and the sixth to ninth reception electrodes RE6 to RE9, are used in a sensing operation, it is possible to minimize a noise component included in the measurement of the moisture level of a user's skin.

Figure 16:
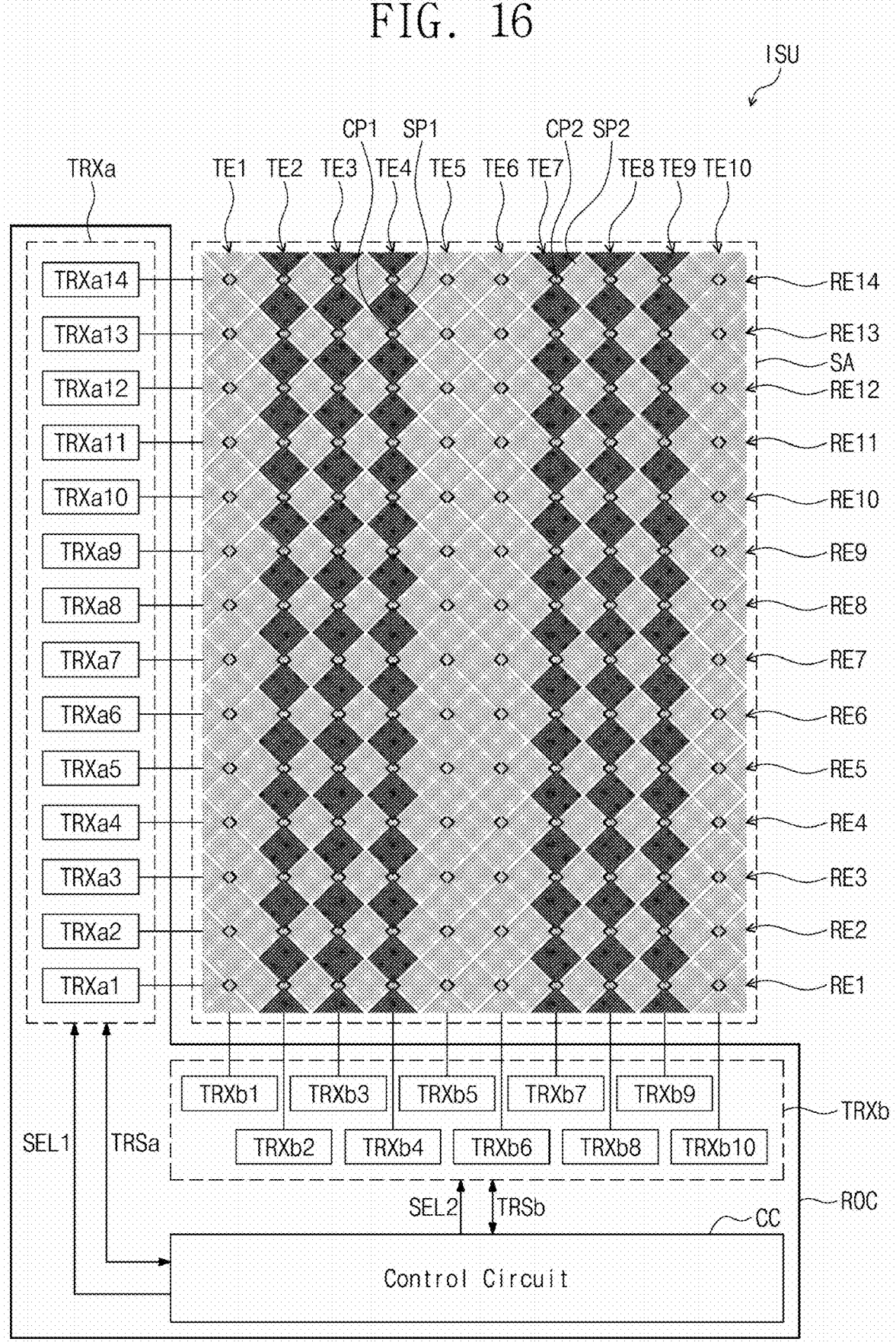
FIG. 16 is a view showing an example of an input sensor operating in a sixth operation mode according to an embodiment.
Figure 17:
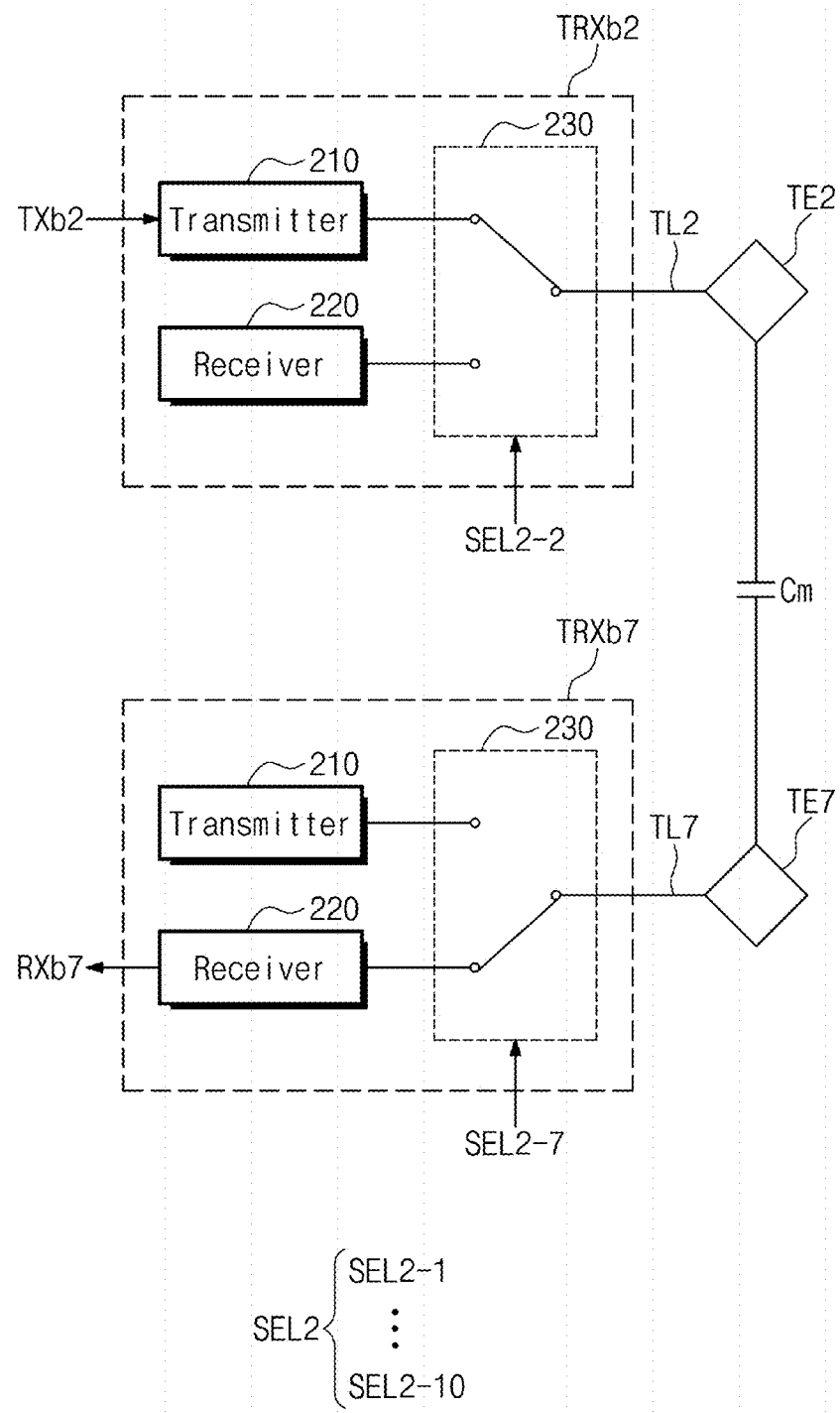
FIG. 17 is a view showing the operation of second transceivers according to a sixth operation mode according to an embodiment.

FIG. 16 is a view showing an example of the input sensor ISU operating in a sixth operation mode according to an embodiment. FIG. 17 is a view showing the operation of second transceivers TRXb2 and TRXb7 according to the sixth operation mode according to an embodiment.

Referring to FIG. 16, the sixth operation mode may be a body composition measurement mode for measuring muscle mass, body fat mass, and/or the like.

When the input sensor ISU operates in the sixth operation mode, some of the first to tenth transmission electrodes TE1 to TE10 or some of the first to fourteenth reception electrodes RE1 to RE14 may be utilized to measure the body composition of a user.

In the sixth operation mode, the input sensor ISU may obtain information on the body composition of a user through the change in mutual capacitance between some of the first to tenth transmission electrodes TE1 to TE10 or the others of the first to tenth transmission electrodes TE1 to TE10.

In an example illustrated in FIG. 16, the input sensor ISU may obtain information on the body composition of a user through the change in mutual capacitance between second to fourth transmission electrodes to TE2 to TE4 and seventh to ninth transmission electrodes TE7 to TE9.

When the input sensor ISU operates in the sixth operation mode, an electric field is formed between the second to fourth transmission electrodes TE2 to TE4 and the seventh to ninth transmission electrodes TE7 to TE9. When the display device DD is brought into contact with a user's body while the input sensor ISU is in operation in the sixth operation mode, the capacitance between the second to fourth transmission electrodes TE2 to TE4 and the seventh to ninth transmission electrodes TE7 to TE9 may be changed according to the user's body composition. For example, in a human body, a skin layer, a subcutaneous fat layer, and a muscle layer each have a different dielectric constant. The dielectric constant of the muscle layer may be smaller than that of the subcutaneous fat layer. Accordingly, as the subcutaneous fat layer is thicker, the capacitance between the second to fourth transmission electrodes TE2 to TE4 and the seventh to ninth transmission electrodes TE7 to TE9 may increase. On the other hand, when the subcutaneous fat layer reduces and the muscle layer becomes thicker, the capacitance between the second to fourth transmission electrodes to TE4 and the seventh to ninth transmission electrodes TE7 to TE9 may decrease.

In the sixth operation mode, the control circuit CC sequentially outputs the second transmission signals TXb2 to TXb4 to the second to fourth transmission electrodes TE2 to TE4, and receives second reception signals RXb7 to RXb9 from the seventh to ninth transmission electrodes TE7 to TE9.

Referring to FIG. 17, during the sixth operation mode, in response to a second selection signal SEL2-2 from the control circuit CC, the switch 230 in a second transceiver TRXb2 electrically connects the second transmission line TL2 to the transmitter 210. The transmitter 210 in the second transceiver TRXb2 may transmit a second transmission signal TXb2 from the control circuit CC to a second transmission electrode TE2 through the second transmission line TL2.

In response to a second selection signal SEL2-7 from the control circuit CC, the switch 230 in a second transceiver TRXb7 electrically connects a seventh transmission line TL7 to the receiver 220.

The second selection signal SEL2 provided from the control circuit CC to the second transmission/reception circuit TRXb (refer to FIG. 16) may include second selection signals SEL2-1 to SEL2-10.

A capacitance Cm between the second transmission electrode TE2 and a seventh transmission electrode TE7 may be transferred to the receiver 220 in the second transceiver TRXb7 through the seventh transmission line TL7 and the switch 230 in the second transceiver TRXb7. The receiver 220 in the second transceiver TRXb7 receives a signal from the seventh transmission electrode TE7, and transfers a second reception signal RXb7 to the control circuit CC.

In the sixth operation mode, the switches 130 (refer to FIG. 9) in the first transceivers TRXa1 to TRXa14 are not connected to any one of the transmitter 110 and the receiver 120. Accordingly, the first to fourteenth reception electrodes RE1 to RE14 may be in a floating state. In another embodiment, the first to fourteenth reception electrodes RE1 to RE14 may receive a ground voltage during the sixth operation mode.

In the same manner, in the sixth operation mode, the switches 230 (refer to FIG. 10) in second transceivers TRXb1, TRXb5, TRXb6, and TRXb10 are not connected to any one of the transmitter 210 and the receiver 220. Accordingly, first, fifth, sixth, and tenth transmission lines TL1, TL5, TL6, and TL10 may be in a floating state. In another embodiment, the first, fifth, sixth, and tenth transmission lines TL1, TL5, TL6, and TL10 may receive a ground voltage during the sixth operation mode.

Figure 18:
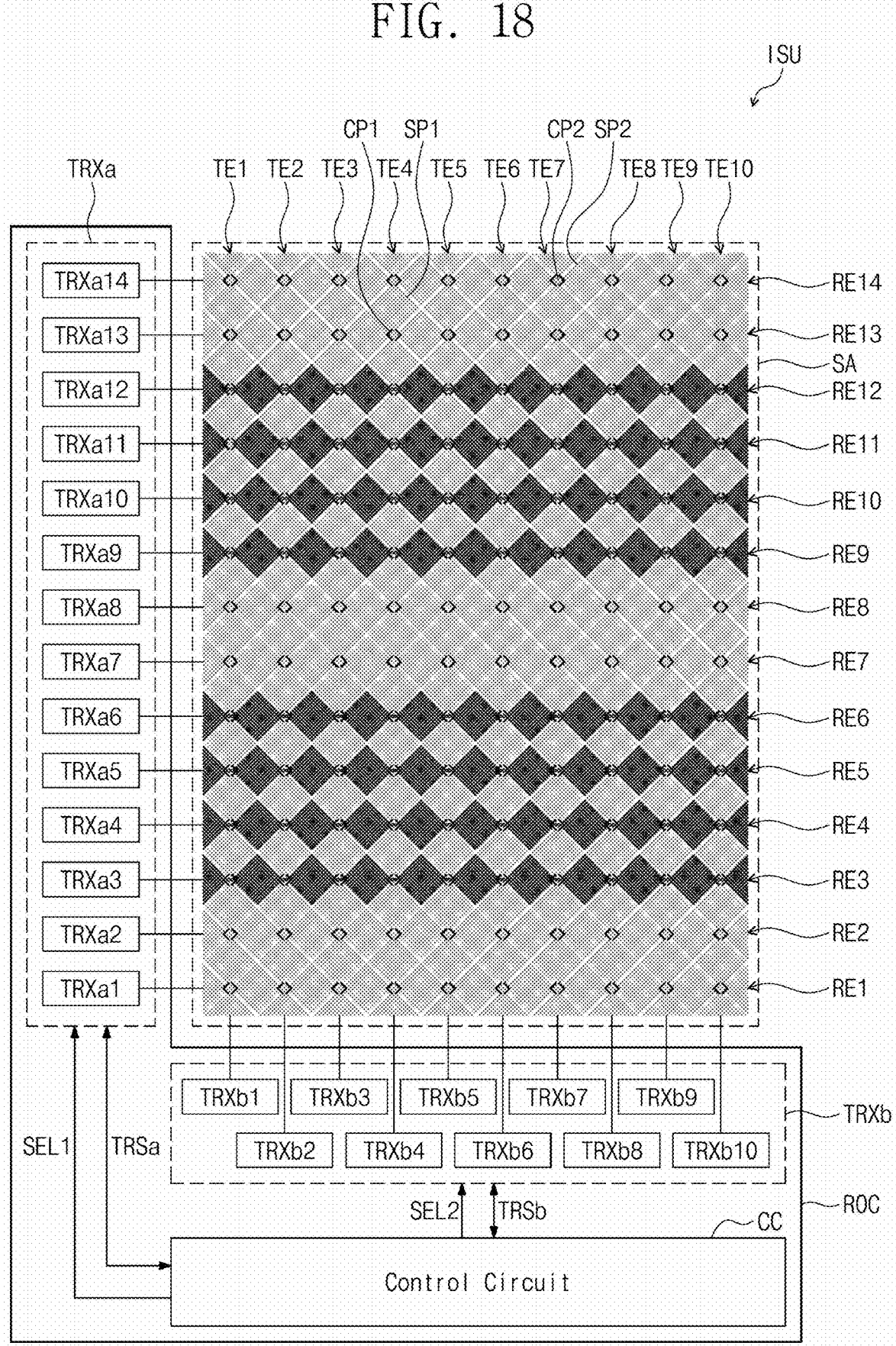
FIG. 18 is a view showing an example of an input sensor operating in a seventh operation mode according to an embodiment.
Figure 19:
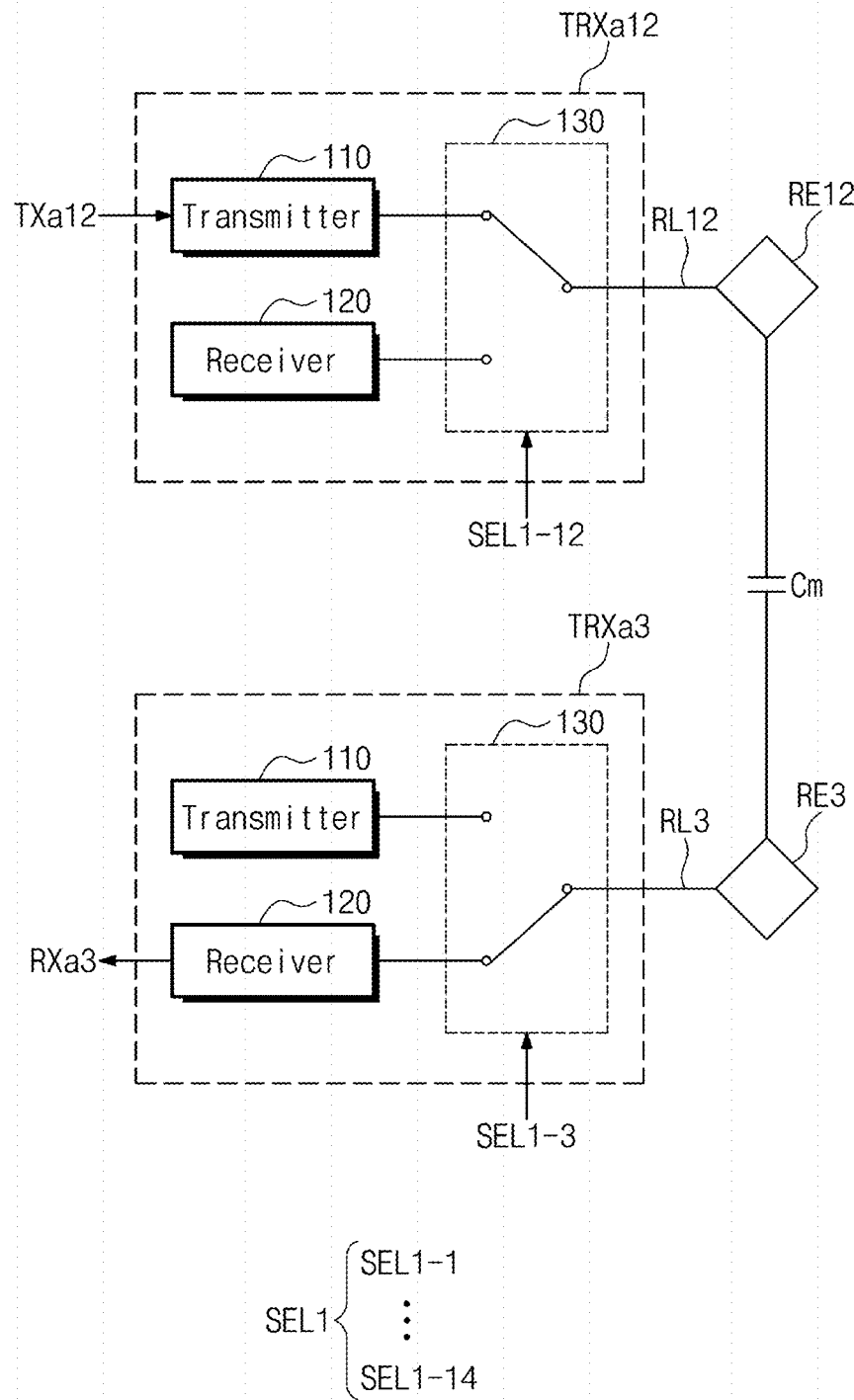
FIG. 19 is a view showing the operation of first transceivers according to a seventh operation mode according to an embodiment.

FIG. 18 is a view showing an example of the input sensor ISU operating in a seventh operation mode according to an embodiment. FIG. 19 is a view showing the operation of first transceivers TRXa3 and TRXa12 according to the seventh operation mode according to an embodiment.

Referring to FIG. 18, the display device DD (refer to FIG. 1) may have a function to measure and analyze the body composition of a user. The display device DD may obtain information on the body composition of the user utilizing the input sensor ISU. The seventh operation mode may be a mode in which the input sensor ISU operates to obtain the information on the body composition of the user. As an example, the body composition may include muscle mass, body fat mass, a moisture level, and/or the like.

When the input sensor ISU operates in the seventh operation mode, some of the first to tenth transmission electrodes TE1 to TE10 or some of the first to fourteenth reception electrodes RE1 to RE14 may be utilized to measure the body composition of a user.

In an example illustrated in FIG. 18, the input sensor ISU may obtain information on the body composition of a user through the change in mutual capacitance between third to sixth reception electrodes RE3 to RE6 and ninth to twelfth reception electrodes RE9 to RE12.

When the input sensor ISU operates in the seventh operation mode, an electric field is formed between the third to sixth reception electrodes RE3 to RE6 and the ninth to twelfth reception electrodes RE9 to RE12. When the display device DD is brought into contact with a user's body while the input sensor ISU is in operation in the seventh operation mode, the capacitance between the third to sixth reception electrodes RE3 to RE6 and the ninth to twelfth reception electrodes RE9 to RE12 may be changed according to the user's body composition.

In the seventh operation mode, the control circuit CC sequentially outputs first transmission signals TXa9 to TXa12 to the ninth to twelfth reception electrodes RE9 to RE12, and receives first reception signals RXa3 to RXa6 from the third to sixth reception electrodes RE3 to RE6.

Referring to FIG. 19, during the seventh operation mode, in response to a first selection signal SEL1-12 from the control circuit CC, the switch 130 in a first transceiver TRXa12 electrically connects a twelfth reception line RL12 to the transmitter 110. The transmitter 110 in the first transceiver TRXa12 may transmit a first transmission signal TXa12 from the control circuit CC to a twelfth reception electrode RE12 through the twelfth reception line RL12.

In response to a first selection signal SEL1-3 from the control circuit CC, the switch 130 in a first transceiver TRXa3 electrically connects a third reception line RL3 to the receiver 120.

The first selection signal SEL1 provided from the control circuit CC to the first transmission/reception circuit TRXa (refer to FIG. 18) may include first selection signals SEL1-1 to SEL14.

A capacitance Cm between the twelfth reception electrode RE12 and a third reception electrode RE3 may be transferred to the receiver 120 in the first transceiver TRXa3 through a third reception line RL3 and the switch 130 in the first transceiver TRXa3. The receiver 120 in the first transceiver TRXa3 receives a signal from the third reception electrode RE3, and transfers a first reception signal RXa3 to the control circuit CC.

In the seventh operation mode, the switches 130 (refer to FIG. 9) in first transceivers TRXa1, TRXa2, TRXa7, TRXa8, TRXa13, and TRXa14 are not connected to any one of the transmitter 110 and the receiver 120. Accordingly, first, second, seventh, eighth, thirteenth, and fourteenth reception lines RL1, RL2, RL7, RL8, RL13, and RL14 may be in a floating state. In another embodiment, the first, second, seventh, eighth, thirteenth, and fourteenth reception lines RL1, RL2, RL7, RL8, RL13, and RL14 may receive a ground voltage during the seventh operation mode.

In the same manner, in the seventh operation mode, the switches 230 (refer to FIG. 10) in the second transceivers TRXb1 to TRXb10 are not connected to any one of the transmitter 210 and the receiver 220. Accordingly, the first to tenth transmission lines TL1 to TL10 may be in a floating state. In another embodiment, the first to tenth transmission lines TL1 to TL10 may receive a ground voltage.

Figure 20:
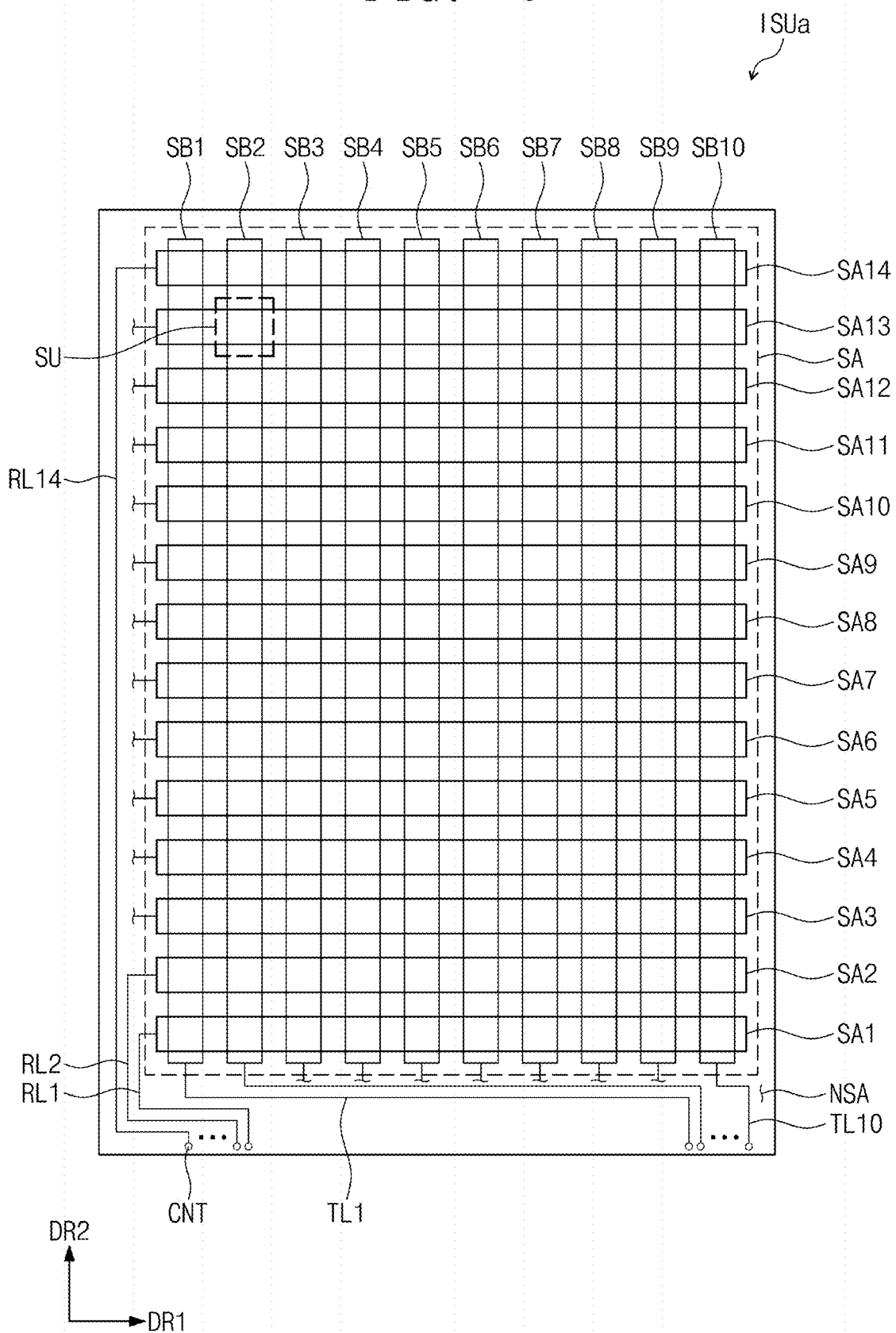
FIG. 20 is a view showing an input sensor according to an embodiment.

FIG. 20 is a view showing an input sensor ISUa according to an embodiment.

Referring to FIG. 20, first sensing electrodes SA1 to SA14 and second sensing electrodes SB1 to SB10 may be disposed in the sensing region SA. The first sensing electrodes SA1 to SA14 are extended along the first direction DR1, and may be spaced apart from each other in the second direction DR2. Each of the second sensing electrodes SB1 to SB10 is extended along the second direction DR2, and may be spaced apart from each other in the first direction DR1. The second sensing electrodes SB1 to SB10 may be arranged intersecting the first sensing electrodes SA1 to SA14. The first sensing electrodes SA1 to SA14 and the second sensing electrodes SB1 to SB10 are insulated from each other.

The first sensing electrodes SA1 to SA14 are electrically connected to the first to fourteenth reception lines RL1 to RL14. The second sensing electrodes SB1 to SB10 are electrically connected to the first to tenth transmission lines TL1 to TL10. An intersection portion of the first sensing electrodes SA1 to SA14 and the second sensing electrodes SB1 to SB10 may be defined as one sensing unit SU.

The input sensor ISUa illustrated in FIG. 20 may operate in the same manner as the input sensor ISU illustrated in FIG. 6.

An input sensor of a display device having the above configuration may sense various inputs, such as biometric information and pen input, as well as a user's touch. Therefore, user convenience may be increased.

Although certain exemplary embodiments and implementations have been described herein, other embodiments and modifications will be apparent from this description. Accordingly, the inventive concepts are not limited to such embodiments, but rather to the broader scope of the accompanying claims and various obvious modifications and equivalent arrangements as would be apparent to one of ordinary skill in the art.

What is claimed is:

1. A display device comprising:
    a display panel configured to display an image;
    an input sensor disposed on the display panel, the input sensor comprising transmission electrodes and reception electrodes electrically insulated from the transmission electrodes; and
    a readout circuit connected to the input sensor,
    wherein:
    the readout circuit comprises:
        a first transmission/reception circuit electrically connected to the reception electrodes;
        a second transmission/reception circuit electrically connected to the transmission electrodes; and a control circuit that, in a body composition measurement mode for measuring a skin moisture level of a user, is configured to:
- transmit a transmission signal to selected ones of the transmission electrodes through the second transmission/reception circuit; and
- receive a reception signal from selected ones of the reception electrodes through the first transmission/reception circuit; and the selected ones of the transmission electrodes and the selected ones of the reception electrodes are less than all of the transmission and reception electrodes, and are pre-selected to minimize a noise component included in the measurement of the skin moisture level of the user.

2. The display device of claim 1, wherein:
the first transmission/reception circuit comprises a plurality of first transceivers respectively corresponding to the reception electrodes; and
each of the plurality of first transceivers is configured to transfer the reception signal from a corresponding reception electrode to the control circuit in response to a first selection signal.

3. The display device of claim 1, wherein:
the second transmission/reception circuit comprises a plurality of second transceivers respectively corresponding to the transmission electrodes; and
each of the plurality of second transceivers is configured to transfer the transmission signal from the control circuit to a corresponding transmission electrode in response to a second selection signal.

* * * * *